United States Patent [19]
Luo et al.

[11] Patent Number: 5,714,509
[45] Date of Patent: Feb. 3, 1998

[54] INHIBITORS OF BACTERIAL SIALIDASE AND METHODS OF MAKING AND USING THE SAME

[75] Inventors: Ming Luo; Clinton L. White, both of Birmingham, Ala.

[73] Assignee: The University of Alabama, Birmingham, Ala.

[21] Appl. No.: 433,290

[22] Filed: May 3, 1995

[51] Int. Cl.$^6$ .......................... A61K 31/34; A61K 31/19; C07D 307/52; C07C 229/64

[52] U.S. Cl. .......................... 514/415; 514/418; 514/553; 514/564; 514/567; 514/472; 549/480; 562/7; 562/11; 562/73; 562/437

[58] Field of Search ........................ 562/437, 7, 11, 562/73; 514/568, 415, 418, 472, 553, 564, 567; 549/480

[56] References Cited

U.S. PATENT DOCUMENTS 5,453,533  9/1995  Luo et al. .......................... 560/142

OTHER PUBLICATIONS

Preston et. al., J. Chem.Soc., pp. 500–504 (1942).

Crennell, S., et al., "Crystal structure of Vibrio cholerae neuraminidase reveals dual lectin–like domains in addition to the catalytic domain", Structure 2:535–544 (1994).

Drzeniek, R., "Viral Bacterial Neuraminidases", Current Topics in Microbiology & Immunology, 59:35–74 (1972).

Warner, T.G., et al., "Photolabelling of Salmonella typhimurium LT2 sialidase,", Biochem. J. 285:957–964 (1992).

Crennell, S.J., et al., "Crystal structure of a bacterial sialidase (from Salmonella typhimurium LT2) shows the same fold as an influenza virus neuraminidase)", Proc. Natl. Acad. Sci. USA 90:9852–9856 (1993).

Hoyer, L.L., et al., "Purification and Properties of Cloned Salmonella typhimurium LT2 Sialidase with Virus–Typical Kinetic Preference for Sialyl α2→3", J. Biochem. 110:462–467 (1991).

Miller, C.A., et al., "Mechanism of Arthrobacter sialophilus Neuraminidase: The Binding of Substrates and Transition–State Analogs", Biochemical and Biophysical Research Communications, 83:1479–1487 (1978).

Holzer, C.T., et al., "Inhibition of sialidases from viral, bacterial and mammalian sources by analogues of 2–deoxy–2,–didehydro–N–acetylneuraminic acid modified at the C–4 position", Glycoconjugate Journal 10:40–44 (1993).

Flashner, M., et al., "The Interaction of Substrate–Related Ketals with Bacterial and Viral Neuraminidases", Archives of Biochemistry and Biophysics 221:188–196 (1983).

Aymard–Henry, M., et al., "Influenzavirus neuraminidase and neurtaminidase–inhibition test procedures", Bull. Wld Hlth Org. 45:119–124 (1971).

Meindl, P., et al., "Inhibition of Neuraminidase Activity by Derivatives of 2–Deoxy–2,3–dehydro–N–acetylneuraminic Acid", Biology 58:457–463 (1974).

Pereira, M.E.A., et al., "The Trypanosoma cruzi Neuraminidase Contains Sequences Similar to Bacterial Neuroaminidases, YWTD Repeats of the Low Density Lipoprotein Receptor, and Type III Modules of Fibronectin", J. Ex. Med. 174:179–191 (1991).

Gross, G.A.M. & Takle, G.B., "The Surface Trans–Sialidase Family of Trypanosoma Cruzi", Annu. Rev. Microbiol. 47:385–411 (1993).

Schenkman, R.P.F., "Mammalian Cell Sialic Acid Enhances Invasion by Trypanosoma cruzi", Infection and Immunity 61:898–902 (1993).

Kleineidam, R.G., et al., "4–Methylumbelliferyl–α–Glycosides od Partially Oacetylated N–Acetylneuraminic Acids as Substrates of Bacterial and Viral Sialidases", Biol. Chem. Hoppe–Seyler 371:715–719 (1990).

Scudder, P., et al., "Enzymatic Characterization of β–D–Galactoside α2,3–trans–Sialidse from Trypanosoma cruzi" The Journal of Biological Chemistry 268:9886–9891 (1993).

Vandekerckhove, F., "Substrate specificity of the Trypanosoma cruzi trans–sialidase", Glycobiology 2:541–548 (1992).

Takle, G.B., & Cross, G.A.M., "An 85–kilodalton surface antigen gene family of Trypanosoma cruzi encodes polypeptides homologous to bacterial neuraminidase", Molecular and Biochemical Parasitology 458:185–198 (1991).

Hall, F.B. & Joiner, K.A., "Developmentally–Regulated Virulence Factors of Trypansoma cruzi and Their Relationship to Evasion of Host Defences" J. Euk. Microbiol. 40(2):207–213 (1993).

Childs, W. D. & Gibbons, R. J. (1990). Selective modulation of bacterial attachment to oral epithelial cells by enzyme activities associated with poor oral hygiene. Journal of Periodontal Research 25(3), 172–8.

(List continued on next page.)

Primary Examiner—Bernard Dentz
Attorney, Agent, or Firm—Needle & Rosenberg, P.C.

[57] ABSTRACT

A sialidase inhibitor of the shown formula I:

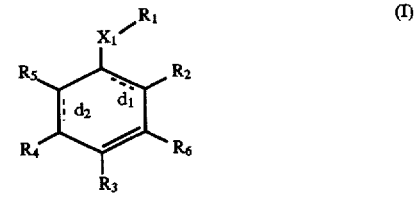

where dashed lines $d_1$ and $d_2$, $X_1$, $R_1$, $R_2$, $R_6$, $R_3$, $R_4$ and $R_5$ are as described in the specification; or an analog, pharmaceutically acceptable salt, or derivative of the inhibitor, with the proviso that the inhibitor is not HNBA GBA or Neu5Ac2en. The inhibitor in a composition with a pharmaceutically acceptable carrier. Methods of making a pharmaceutical composition of an acceptable carrier and the inhibitor. Methods of inhibiting sialidase and methods of treating and preventing bacterial or trypanosomal infection using the inhibitor.

14 Claims, 8 Drawing Sheets

OTHER PUBLICATIONS

Liljemark, W. F., Bloomquist, C. G., Fenner, L. J., Antonelli, P. J. & Coulter, M.C. (1989). Effect of neuraminidase on the adherence to salivary pellicle of *Streptococcus sanguis* and *Streptococcus mitis*. *Caries Research* 23:141–145.

Nakato, H., Shinomiya, K. & Mikawa, H. (1986). Possible role of neuraminidase in the pathogenesis of arteritis and thrombocytopenia induced in rats by *Erysipelothrix rhusiopathiae*. *Pathology, Research & Practice* 181(3), 311–9.

Cacalano, G., Kays, M., Saiman, L. & Prince, A. (1992). Production of the *Pseudomonas aeruginosa* neuraminidase is increased under hypersmolar conditions and is regulated by genes involved in alginate expression. *Journal of clinical Investigation* 89(6), 1866–74.

Costello, A. H., Cisar, J.O., Kolenbrander, P.E. & Gabriel, O. (1979). Neuraminidase-dependent hamagglutination to human erythrocytes by human strains of *Actinomyces viscosus* and *Actinomyces naeslundii*. *Infection & Immunity* 26(2), 563–72.

Guzman, C. A., Plate, M. & Pruzzo, C. (1990). Role of neuraminidase-dependent adherence in *Bacteroides fragilis* attachment to human epithelial cells. *FEMS Microbiology Letters* 71, 187–92.

Briselden, A. M., Moncla, B. J., Stevens, C. E. & Hillier, S. L. (1992). Sialidases (-neuraminidase) in bacterial vaginosis and bacterial vaginosis-associated microflora. *Journal of Clinical Microbiology* 30(3), 663–6.

LaMarco, K. K., Diven, W. F. & Glew, R. H. (1986). Experimental alteration of chinchilla middle ear mucosae by bacterial neuraminidase. *Annals of Otology, Rhinology & Laryngology* 95(3 Pt 1), 304–8.

Marchand, N.W., Kishore, G.S. & Carubelli, R. (1978). Neuraminidase activity in the blood and liver of arthritic rats. *Experimental & Molecular Pathology* 29(3), 273–80.

Seger, R., Joller, P., Baerlocher, K., Kenny, A., Dulake, C., Leumann, E., Spierig, M. & Hitzig, W. H. (1980). Hemolytic-uremic syndrome associated with neuraminidase-producing microorganisms: treatment by exchange transfusion. *Helvetica Paediatrica Acta* 35(4), 359–67.

Milligan, T. W., Baker, C. J., Straus, D. C. & Mattingly, S. J. (1978). Association of elevated levels of extracellular neuraminidase with clinical isolates of type III group B streptococci. *Infection & Immunity* 21(3), 738–46.

Mosquera, J. & Rodriguez–Iturbe, B. (1984). Extracellular neuraminidase production of streptococci associated with acute nephritis. *Clinical Nephrology* 21(1), 21–8.

Hoffler, U., Gloor, M. & von Nicolai, H. (1981). Neuraminidase production by Propionibacterium acnes-strains isolated from patients with acne vulgaris, seborrheic eczema and healthy subjects. *Zentralblatt Fur Bakteriologie, Mikrobiologie Und Hygiene*–250(1–2), 122–6.

INHIBITORS OF BACTERIAL SIALIDASE AND METHODS OF MAKING AND USING THE SAME

GOVERNMENT INTEREST

This application has been supported by a grant from the National Institutes of Health, AI-31888 (M.L) and a grant from the National Aeronautics and Space Administration, NAGW-813 (P.I. Dr. Delucas).

BACKGROUND

1. Field of the Invention

This invention relates to inhibitors of bacterial sialidases. In particular, this invention provides novel inhibitors to bacterial sialidases, methods of making the inhibitors, methods of treatment using the inhibitors and methods of prophylaxis from bacterial infection using the inhibitors.

2. Background of the Invention

Sialidases (acylneuraminyl hydrolases, EC 3.2.1.18), also known as neuraminidases, are enzymes which cleave the α-ketosidic bond between a terminal sialic acid residue and an aglycon moiety. The aglycon is usually the penultimate sugar residue of a glycoconjugate or glycoprotein carbohydrate chain. The first sialidase was purified and characterized from the influenza virus and the bacteria *Vibrio cholerae* [Gottschalk, A. (1957). Neuraminidase: The Specific Enzyme of Influenza Virus and *Vibrio cholerae*. Biochim Biophys Acta., 23, pp. 645–646]. Today, sialidases specific for varying ketosidic linkages have been identified in viruses, bacteria, parasites, and mammals. They play a critical role in viral, bacterial, and protozoa biology by mediating metabolism, adherence, and infection, and are important regulators of alternate complement pathway activation, red blood cell destruction, cell growth, cell adhesion, and tumor metastasis in mammalian systems.

Therefore, the development of sialidase inhibitors could lead to a better understanding of these mechanisms. Also, given the wide prevalence and important role of sialidases in microbial infection, it is highly desirable to develop sialidase inhibitors to be used as anti-bacterial and anti-trypanosomal agents.

Though sialidases have long been identified in bacteria, the last twenty years have seen an explosion of bacterial sialidases purified and characterized due to the advance of molecular biological techniques. The explosion has also shed light on sialidase's role in bacterial metabolism, adherence, infection, and pathogenicity. Except for the active site, the bacterial sialidases do not exhibit an amino acid sequence similarity to the viral sialidases. Another characteristic of bacterial sialidases is the presence of non-sialidase related domains in the protein. These domains have other activities or functions which are beneficial to the bacteria. Many bacterial sialidases are membrane anchored, like the viral sialidases, while others are excreted extracellularly by the bacterium. Bacterial sialidases fall into two further subgroups based upon divalent metal requirements. The sialidase subgroup that requires a metal ion is represented by the *Vibrio cholerae* sialidase. The subgroup that does not require a metal ion for activity is represented by several bacterial sialidases, such as *Clostridium perfringens, Clostridium sordelli, Micromonospora viridifaciens*, and *Salmonella typhimurium* among others. In addition to the high degree of sequence homology within the subgroup, the non-metal requiring sialidases also show a large amount of similarity to the N-terminal trans- sialidase domain of the trypanosomal trans-sialidase enzyme. The crystal structure for *Salmonella typhimurium* sialidase has been solved [Crennell, S. J., Garman, E. F., Laver, W. G., Vimr, E. R. & Taylor, G. L. (1993), The crystal structure of a bacterial sialidase (from Salmonella typhimurium LT2) shows the same fold as an influenza virus neuraminidase. *Proc Nat Acad of Sci USA*., 90, pp. 9852–6].

SUMMARY OF THE INVENTION

The current invention relates to the structure-based design, synthesis and in vitro evaluation of non-carbohydrate inhibitors of bacterial sialidase. Using structure-based drug design, a broad class of novel, potent, and selective inhibitors of bacterial sialidase has been developed.

The present invention provides a sialidase inhibitor as set forth in General Structure I:

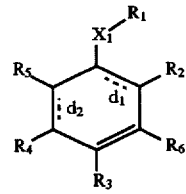

General Structure (I)

wherein the dashed lines $d_1$ and $d_2$ are independently unsaturations or saturations and the core ring is cyclic or heterocyclic with one to two heteroatoms of O, N, or S; $X_1$ is CO, $SO_2$, NH, $CH_2$, S, or O; $R_1$ is $NH_2$, SH, $OCH_3$, halide, $COA_1$, where $A_1$ is branched or unbranched, alkyl, alkenyl or alkynyl of from 1 to 5 carbons, and $A_1$ is unsubstituted or substituted independently with one or more substitutions of OH, SH, $NH_2$ or halide, a branched or unbranched, alkyl, alkenyl or alkynyl of from 1 to 6 carbons, unsubstituted or substituted independently with one or more substitutions of OH, SH, $NH_2$ or halide, or a 5-, 6-, or 7-membered first ring, saturated or unsaturated, unsubstituted or substituted independently with one or more substitutions of (a) OH or (b) a branched or unbranched, alkyl, alkenyl or alkynyl of from 1 to 6 carbons, unsubstituted or substituted independently with one or more substitutions of OH, SH, $NH_2$ or halide, where the 5-, 6-, or 7-membered first ring is cyclic or heterocyclic with one to two heteroatoms of O, N, or S; $R_2$ and $R_6$ are independently H, OH, SH, $NH_2$, halide, or $A_2$ where $A_2$ is alkyl, alkoxy, alkenyl, alkenoxy, alkynyl, or alkynoxy, or alkanol, alkenol, or alkynol of one or more OH moieties on the alkanol, alkenol, or alkynol, where $A_2$ is unbranched or branched, of from 1 to 4 carbons, and $A_2$ is unsubstituted or substituted independently with one or more substitutions of $NH_2$, COOH, halide, SH, OH, or guanidinium; $R_3$ is $COO^-$, $POO^-$, $BOO^-$ or $SOO^-$ where the corresponding cation is H or a salt; and wherein A) $R_4$ is H and $R_5$ is $NO_2$; B) $R_4$ is H, OH, SH, halide, COOH, guanidinium, or alkanol of one or more OH moieties, branched or unbranched, of from 1 to 4 carbons, and $R_5$ is $A_3$ where $A_3$ is alkyl, alkoxy, alkenyl, alkenoxy, alkynyl, or alkynoxy, or alkanol, alkenol, or alkynol of one or more OH moieties on the alkanol, alkenol, or alkynol, where $A_3$ is unbranched or branched, of from 1 to 4 carbons, and $A_3$ is unsubstituted or substituted independently with one or more substitutions of $NH_2$, COOH, halide, SH, OH, or guanidinium; or C) $R_4$ is C, CH, or $CH_2$ and $R_5$ is CH, or $CH_2$, and $R_4$ forms a 4-, 5-, or 6-membered second ring with $R_5$, where the second ring is saturated, partially unsaturated or fully unsaturated, cyclic or heterocyclic with one to two heteroatoms of O, N, or S substituted for any second ring carbon, and $R_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and $R_5$ is substituted with $A_4NH_3^+$, where $A_4$ is alkyl, alkenyl or alkynyl, or alkanol or alkenol of one or more OH moieties on the alkanol or alkenol, of from 1 to 3 carbons, and, for the 5- or 6-membered second ring, the intermediate second ring carbons between $R_4$ and $R_5$ are independently unsubstituted or substituted with one or more substitutions of OH, or alkanol, alkenol or alkynol of one or more OH moieties on the alkanol, alkenol, or alkynol, branched or unbranched, of from 1 to 4 carbons; or an analog, pharmaceutically acceptable salt, or derivative of the inhibitor of general structure I, with the proviso that when $X_1$ is NH, $R_1$ is $COCH_3$, $R_2$ is OH, $R_6$ is H, and $R_3$ is $COO^-$, (a) $R_5$ is not $NO_2$ or $NHC(NH)NH_2$ when $R_4$ is H and $d_1$ and $d_2$ are unsaturations and (b) $R_5$ is not $CH(OH)CH(OH)CH_2(OH)$ when $d_1$ and $d_2$ are saturations and the core ring is substituted with the heteroatom O at the core ring carbon adjacent to $R_4$.

The present invention also discloses pharmaceutical compositions for inhibiting sialidase, comprising an inhibiting effective amount of a compounds of the invention and a pharmaceutically acceptable carrier.

In yet another embodiment, the present invention discloses a method of inhibiting sialidase, comprising administering to a subject an inhibiting effective amount of a compound of the invention.

In a further embodiment, the present invention presents a method of making a composition for inhibiting sialidase, comprising admixing an inhibiting effective amount a compound of the invention with a pharmaceutically acceptable carrier In yet another embodiment, the present invention discloses a method of preventing bacterial or trypanosomal infection, comprising administering to a subject preventative effective amount a compound of the present invention.

Finally, the present invention discloses, in yet another preferred embodiment, a method of treating bacterial or trypanosomal infection, comprising administering to a subject treatment effective amount a compound of the invention.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that the both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
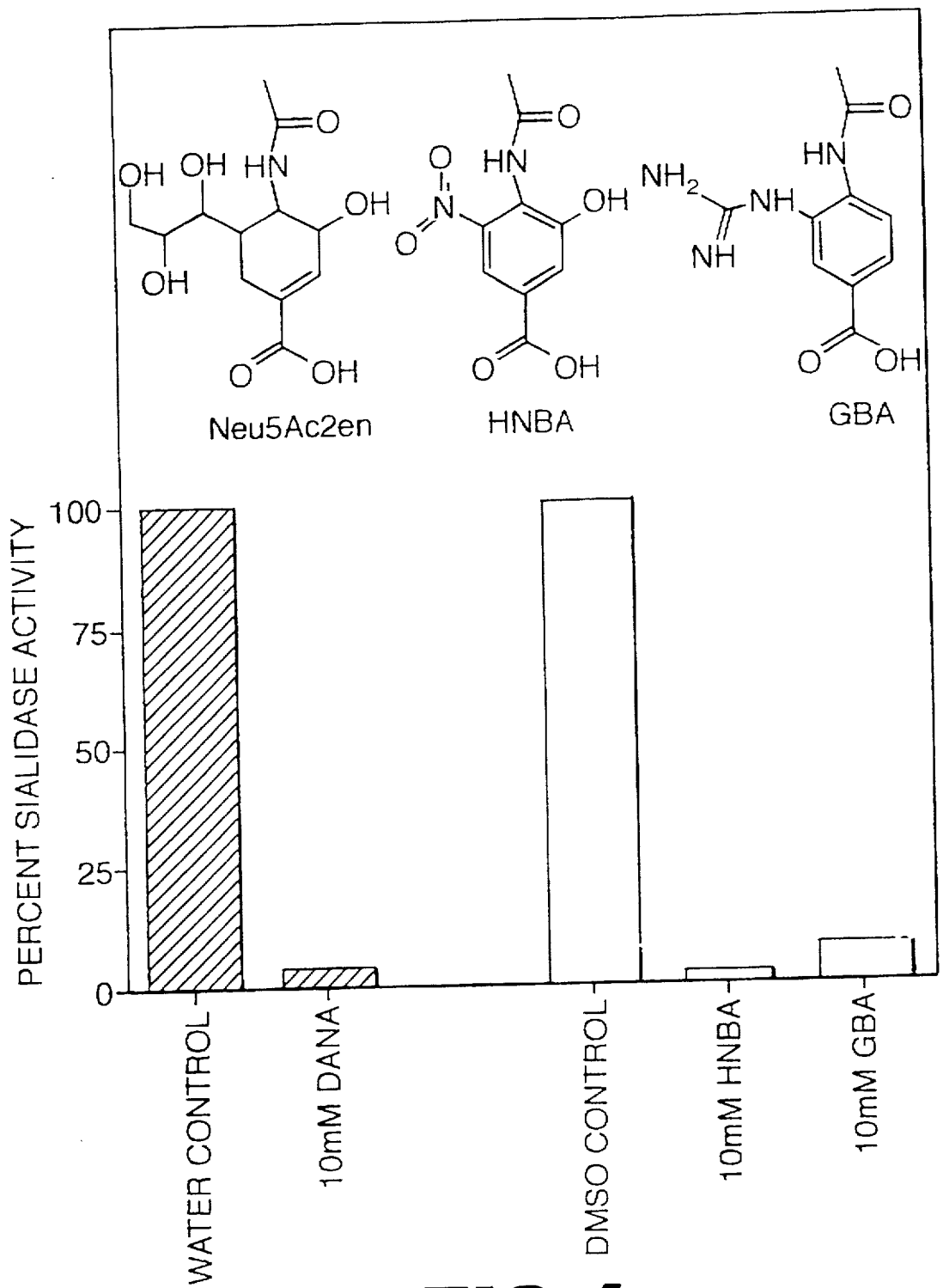
FIG. 1 shows a graph of the inhibitory activity and the chemical structures of Neu5Ac2en, HNBA and GBA.

The present invention may be understood more readily by reference to the following detailed description of preferred embodiments of the invention and the Examples included therein and to the Figures and their previous and following description.

Before the present compounds, compositions and methods are disclosed and described, it is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

In this specification and in the claims which follow, reference will be made to a number of terms which shall be defined to have the following meanings.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, and the like. Preferred alkyl groups herein contain from 1 to 6, or more preferably 1 to 4, carbon atoms The term "lower alkyl" intends an alkyl group of from one to six carbon atoms, preferably from one to four carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing from one to six, more preferably from one to four, carbon atoms Likewise, the terms "alkenoxy" and "alkynoxy" as used herein intend an alkenyl or alkynyl group bound through a single, terminal ether linkage; that is, an "alkenoxy" or "alkynoxy" group may be defined as —OR where R is alkenyl or alkynyl as defined above.

The term "alkenyl" as used herein intends a mono-unsaturated or poly-unsaturated hydrocarbon group of 2 to 24 carbon atoms Preferred groups within this class contain 2 to 12 carbon atoms Likewise, the term "alkynyl" as used herein intends a hydrocarbon group of 2 to 24 carbon atoms containing at least one triple bond Preferred groups within this class contain 2 to 12 carbon atoms The term "halide" is used to refer to any halogen including, F, Cl, I, or Br.

The terms "cyclic" and "heterocyclic" refer to rings where, respectively, none or one or more of the carbon atoms have been replaced. For instance, for a "heterocyclic" ring, a carbon in the ring may be preferably substituted with N, O, or S Such atoms which are substituted are herein called "heteroatoms." One of skill in the art would recognize that other suitable heteroatoms exist. The term "core ring" is used to refer to the base six-membered ring depicted in general structure I. The terms "saturation" and "unsaturation" are used to describe whether, between a particular pair of atoms, a single or double bond exists. Single bonds are termed "saturations" and double bonds are termed "unsaturations" One of skill in the art would recognize that triple bonds could also constitute "unsaturations" Furthermore, the terms "saturated" and "partially unsaturated" and "fully unsaturated" are used to refer to the presence or lack of unsaturations in a particular ring For instance, cyclohexane would be considered a "saturated" compound On the other hand cyclohexene would be "partially unsaturated" due to the presence of one unsaturation Finally, benzene is "fully unsaturated" due to the presence of the maximum, three, unsaturations. The terms "alkanol", "alkenol" and "alkynol", as used herein, refer to the alcohol versions of respective alkanes, alkenes and alkynes. The alcohols may contain one or more OH moieties. Furthermore, the alcohols may be branched or straight and the OH moieties may be present at the terminal carbons or elsewhere along the carbon chain. More than one OH group may be substituted at any particular carbon Examples of "alkanols" are methanol, ethanol, $CH_3CH(OH)_2$, etc Examples of alkenols include $CH_2CHOH$, $CH_3CH_2CHOH$, etc. An example of an alkynol is $CH_3CH_2CCOH$. As used in the claims, a substitution of an alkanol implies that one of the hydrogens is removed at the linking atom and that atom is bonded to the entity having the substitution. The same interpretation applies to all other moieties described in this specification where the context requires such interpretation.

As used herein, "subject" is intended to cover humans, mammals and other animals which are susceptible to bacteria in any fashion.

By the term "effective amount" of a compound as provided herein is meant a nontoxic but sufficient amount of the compound to provide the desired utility. For instance, for inhibition of sialidase, the effective amount is the amount which provides clinically meaningful inhibition of sialidase in a subject. As will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

By "pharmaceutically acceptable" is meant a material that is not biologically otherwise undesirable, i.e., the material may be administered to an individual along with the selected bicyclic compound without causing any undesirable biological effects or interacting in a deleterious manner with any of the other components of the pharmaceutical composition in which it is contained.

Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to about 100° C., preferably at room temperature. The molar ratio of compounds of general structure I to base used are chosen to provide the ratio desired for any particular salts. For preparing, for example, the ammonium salts of the free acid starting material, the starting material can be treated with approximately one equivalent of pharmaceutically acceptable base to yield a neutral salt. When calcium salts are prepared, approximately one-half a molar equivalent of base is used to yield a neutral salt, while for aluminum salts, approximately one-third a molar equivalent of base will be used "Salt" is further defined elsewhere herein.

As used herein, and without limitation, the term "analog" is used to refer to any compound which has structural similarity to the compounds of the invention and would be expected, by one skilled in the art, to exhibit the same or similar utility as the claimed compounds.

As used herein, and without limitation, the term "derivative" is used to refer to any compound which has a structure derived from the structure of the compounds of the present invention and whose structure is sufficiently similar to those disclosed herein and based upon that similarity, would be expected, by one skilled in the art, to exhibit the same or similar activities and utilities as the claimed compounds.

With these definitions in mind, the present invention provides a sialidase inhibitor of formula I:

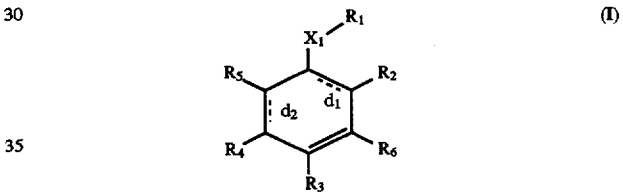

wherein the dashed lines $d_1$ and $d_2$ are independently unsaturations or saturations and the core ring is cyclic or heterocyclic with one to two heteroatoms of O, N, or S; $X_1$ is CO, $SO_2$, NH, $CH_2$, S, or O; $R_1$ is $NH_2$, SH, $OCH_3$, halide, $COA_1$, where $A_1$ is branched or unbranched, alkyl, alkenyl or alkynyl of from 1 to 5 carbons, and $A_1$ is unsubstituted or substituted independently with one or more substitutions of OH, SH, $NH_2$ or halide, a branched or unbranched, alkyl, alkenyl or alkynyl of from 1 to 6 carbons, unsubstituted or substituted independently with one or more substitutions of OH, SH, $NH_2$ or halide, or a 5-, 6-, or 7-membered first ring, saturated or unsaturated, unsubstituted or substituted independently with one or more substitutions of (a) OH or (b) a branched or unbranched, alkyl, alkenyl or alkynyl of from 1 to 6 carbons, unsubstituted or substituted independently with one or more substitutions of OH, SH, $NH_2$ or halide, where the 5-, 6-, or 7-membered first ring is cyclic or heterocyclic with one to two heteroatoms of O, N, or S; $R_2$ and $R_6$ are independently H, OH, SH, NH:, halide, or $A_2$ where $A_2$ is alkyl, alkoxy, alkenyl, alkenoxy, alkynyl, or alkynoxy, or alkanol, alkenol, or alkynol of one or more OH moieties on the alkanol, alkenol, or alkynol, where $A_2$ is unbranched or branched, of from 1 to 4 carbons, and $A_2$ is unsubstituted or substituted independently with one or more substitutions of $NH_2$, COOH, halide, SH, OH, or guanidinium; $R_3$ is $COO^-$, $POO^-$, $BOO^-$ or $SOO^-$ where the corresponding cation is H or a salt; and wherein A) $R_4$ is H and $R_1$ is $NO_2$; B) $R_4$ is H, OH, SH, halide, COOH, guanidinium, or alkanol of one or more OH moieties, branched or unbranched, of from 1 to 4 carbons, and $R_5$ is $A_3$ where $A_3$ is alkyl, alkoxy, alkenyl, alkenoxy, alkynyl, or alkynoxy, or alkanol, alkenol, or alkynol of one or more OH moieties on the alkanol, alkenol, or alkynol, where $A_3$ is unbranched or branched, of from 1 to 4 carbons, and $A_3$ is unsubstituted or substituted independently with one or more substitutions of $NH_2$, COOH, halide, SH, OH, or guanidinium; or C) $R_4$ is C, CH, or $CH_2$ and $R_5$ is CH, or $CH_2$, and $R_4$ forms a 4-, 5-, or 6-membered second ring with $R_5$, where the second ring is saturated, partially unsaturated or fully unsaturated, cyclic or heterocyclic with one to two heteroatoms of O, N, or S substituted for any second ring carbon, and $R_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and $R_5$ is substituted with $A_4NH_3^+$, where $A_4$ is alkyl, alkenyl or alkynyl, or alkanol or alkenol of one or more OH moieties on the alkanol or alkenol, of from 1 to 3 carbons, and, for the 5- or 6-membered second ring, the intermediate second ring carbons between $R_4$ and $R_5$ are independently unsubstituted or substituted with one or more substitutions of OH, or alkanol, alkenol or alkynol of one or more OH moieties on the alkanol, alkenol, or alkynol, branched or unbranched, of from 1 to 4 carbons; or an analog, pharmaceutically acceptable salt, or derivative of the inhibitor of the formula I, with the proviso that when $X_1$ is NH, $R_1$ is $COCH_3$, $R_2$, is OH, $R_6$ is H, and $R_3$ is $COO^-$, (a) $R_5$ is not $NO_2$ or NHC(NH)$NH_2$ when $R_4$ is H and $d_1$ and $d_2$ are unsaturations and (b) $R_5$ is not $CH(OH)CH(OH)CH_2(OH)$ when $d_1$ and $d_2$ are saturations and the core ring is substituted with the heteroatom O at the core ring carbon adjacent to $R_4$.

In a preferred embodiment, $R_4$ is H and $R_5$ is $NO_2$. In another preferred embodiment, $R_4$ is H, OH, SH, halide, COOH, guanidinium, or alkanol of one or more OH moieties, branched or unbranched, of from 1 to 4 carbons, and $R_5$ is $A_3$ where $A_3$ is alkyl, alkoxy, alkenyl, alkenoxy, alkynyl, or alkynoxy, or alkanol, alkenol, or alkynol of one or more OH moieties on the alkanol, alkenol, or alkynol, where $A_3$ is unbranched or branched, of from 1 to 4 carbons, and $A_3$ is unsubstituted or substituted independently with one or more substitutions of $NH_2$, COOH, halide, SH, OH, or guanidinium. In yet another preferred embodiment, $R_4$ is C, CH, or $CH_2$ and $R_5$ is CH, or $CH_2$, and $R_4$ forms a 4-, 5-, or 6-membered second ring with $R_5$, where the second ring is saturated, partially unsaturated or fully unsaturated, cyclic or heterocyclic with one to two heteroatoms of O, N, or, S substituted for any second ring carbon, and $R_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and $R_5$ is substituted with $A_4NH_3^+$, where $A_4$ is alkyl, alkenyl or alkynyl, or alkanol or alkenol of one or more OH moieties on the alkanol or alkenol, of from 1 to 3 carbons, and, for the 5- or 6-membered second ring, the intermediate second ring carbons between $R_4$ and $R_5$ are independently unsubstituted or substituted with one or more substitutions of OH, or alkanol, alkenol or alkynol of one or more OH moieties on the alkanol, alkenol, or alkynol, branched or unbranched, of from 1 to 4 carbons.

In a further preferred embodiment, the present invention provides the inhibitors of the claimed invention where $R_4$ is C and $R_5$ is C and $R_4$ forms a 4-membered second ring with $R_5$, where the second ring is saturated, partially unsaturated or fully unsaturated, cyclic or heterocyclic with one to two heteroatoms of O, N, or S substituted for any second ring carbon, and $R_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and $R_5$ is substituted with $A_4NH_3^+$, where $A_4$ is alkyl, alkenyl or alkynyl, or alkanol or alkenol of one or more OH moieties on the alkanol or alkenol, of from 1 to 3 carbons. In another preferred embodiment, $R_4$ is C, CH and $R_5$ is CH, or $CH_2$, and $R_4$ forms a 5-membered second ring with $R_5$, where the second ring is saturated, partially unsaturated or fully unsaturated, cyclic or heterocyclic with one to two heteroatoms of O, N, or S substituted for any second ring carbon, and $R_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and $R_r$ is substituted with $A_4NH_3^+$, where $A_4$ is alkyl, alkenyl or alkynyl, or alkanol or alkenol of one or more OH moieties on the alkanol or alkenol, of from 1 to 3 carbons, and the intermediate second ring carbon between $R_4$ and $R_5$ is independently unsubstituted or substituted with one or more substitutions of OH, or alkanol, alkenol or alkynol of one or more OH moieties on the alkanol, alkenol, or alkynol, branched or unbranched, of from 1 to 4 carbons. In a further preferred embodiment, $R_4$ is C, CH, or $CH_2$ and $R_5$ is CH, or $CH_2$, and $R_4$ forms a 6-membered second ring with $R_5$, where the second ring is saturated, partially unsaturated or fully unsaturated, cyclic or heterocyclic with one to two heteroatoms of O, N, or S substituted for any second ring carbon, and $R_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and $R_5$ is substituted with $A_4NH_3^+$, where $A_4$ is alkyl, alkenyl or alkynyl, or alkanol or alkenol of one or more OH moieties on the alkanol or alkenol, of from 1 to 3 carbons, and the intermediate second ring carbons between $R_4$ and $R_5$ are independently unsubstituted or substituted with one or more substitutions of OH, or alkanol, alkenol or alkynol of one or more OH moieties on the alkanol, alkenol, or alkynol, branched or unbranched, of from 1 to 4 carbons.

In further preferred embodiments, the present invention provides the sialidase inhibitor wherein $X_1$ is NH; $R_1$ is a furanyl- or phenyl-, unsubstituted or substituted with OH, $CH_3$ or glycerol; $R_2$ is OH or $NH_2$; $R_6$ is H; $R_3$ is $COO^-$ where the corresponding cation is H or a salt; $R_4$ is H; and $R_5$ is $NO_2$. In yet another preferred embodiment, the present invention discloses a sialidase inhibitor wherein $X_1$ is NH; Rx is $CH_3CO$; $R_2$ is OH or $NH_2$; $R_6$ is H; $R_5$ is $COO^-$ where the corresponding cation is H or a salt; $R_4$ is H, OH, SH, halide, COOH, guanidinium, or alkanol of one or more OH moieties, branched or unbranched, of from 1 to 4 carbons, and $R_5$ is $A_3$ where $A_3$ is alkyl, alkoxy, alkenyl, alkenoxy, alkynyl, or alkynoxy, or alkanol, alkenol, or alkynol of one or more OH moieties on the alkanol, alkenol, or alkynol, where $A_3$ is unbranched or branched, of from 1 to 4 carbons, and $A_3$ is unsubstituted or substituted independently with one or more substitutions of $NH_2$, COOH, halide, SH, OH, or guanidinium. In yet another preferred embodiment, the present invention discloses a sialidase inhibitor wherein $X_1$ is NH; $R_1$ is $CH_3CO$; $R_2$ is OH or $NH_2$; $R_3$ is H; $R_3$ is $COO^-$ where the corresponding cation is H or a salt; $R_1$ is C; and $R_5$ is C, and $R_4$ forms a 4-membered second ring with $R_5$, where the second ring is saturated, partially unsaturated or fully unsaturated, cyclic or heterocyclic with one to two heteroatoms of O, N, or S substituted for any second ring carbon, and $R_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and $R_5$ is substituted with $A_4NH_3^+$, where $A_4$ is alkyl, alkenyl or alkynyl, or alkanol or alkenol of one or more OH moieties on the alkanol or alkenol, of from 1 to 3 carbons. In a further embodiment, the invention provides a sialidase inhibitor wherein $X_1$ is NH; $R_1$ is $CH_3CO$; $R_2$ is OH or $NH_2$; $R_6$ is H; $R_3$ is $COO^-$ where the corresponding cation is H or a salt; $R_4$ is C, CH; and $R_5$ is CH, or $CH_2$, and $R_4$ forms a 5-membered second ring with $R_5$, where the second ring is saturated, partially unsaturated or fully unsaturated, cyclic or heterocyclic with one to two heteroatoms of O, N, or S substituted for any second ring carbon, and $R_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and $R_5$ is substituted with $A_4NH_3^+$, where $A_4$ is alkyl, alkenyl or alkynyl, or alkanol or alkenol of one or more OH moieties on the alkanol or alkenol, of from 1 to 3 carbons, and the intermediate second ring carbon between $R_4$ and $R_5$ is independently unsubstituted or substituted with one or more substitutions of OH, or alkanol, alkenol or alkynol of one or more OH moieties on the alkanol, alkenol, or alkynol, branched or unbranched, of from 1 to 4 carbons. In yet another preferred embodiment, the present invention discloses a sialidase inhibitor wherein $X_1$ is NH; $R_1$ is $CH_3CO$; $R_2$ is OH or $NH_2$; $R_6$ is H; $R_3$ is $COO^-$ where the corresponding cation is H or a salt; $R_4$ is C, CH, or $CH_2$; and $R_5$ is CH, or $CH_2$, and $R_4$ forms a 6-membered second ring with $R_5$, where the second ring is saturated, partially unsaturated or fully unsaturated, cyclic or heterocyclic with one to two heteroatoms of O, N, or S substituted for any second ring carbon, and $R_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and $R_5$ is substituted with $A_4NH_3^+$, where $A_4$ is alkyl, alkenyl or alkynyl, or alkanol or alkenol of one or more OH moieties on the alkanol or alkenol, of from 1 to 3 carbons, and the intermediate second ring carbons between $R_4$ and $R_5$ are independently unsubstituted or substituted with one or more substitutions of OH, or alkanol, alkenol or alkynol of one or more OH moieties on the alkanol, alkenol, or alkynol, branched or unbranched, of from 1 to 4 carbons.

In a further preferred embodiment, the present invention discloses a sialidase inhibitor wherein dashed lines $d_1$ and $d_2$ are both unsaturations, $X_1$ is NH; $R_1$ is unsubstituted furanyl-; $R_2$ is OH; $R_6$ is H; $R_3$ is $COO^-$ where the corresponding cation is H or a salt; $R_4$ is H; and $R_5$ is $NO_2$.

Another preferred embodiment discloses a sialidase inhibitor wherein dashed lines $d_1$ and $d_2$ are both unsaturations, $X_1$ is NH; $R_1$ is mono- or dimethyl-substituted furanyl-; $R_2$ is OH; $R_6$ is H; $R_3$ is $COO^-$ where the corresponding cation is H or a salt; $R_4$ is H; and $R_5$ is $NO_2$.

In yet another preferred embodiment, the present invention discloses a sialidase inhibitor wherein dashed lines $d_1$ and $d_2$ are both unsaturations, $X_1$ is NH; $R_1$ is p-phenylhydroxyl-; $R_2$ is OH; $R_6$ is H; $R_3$ is $COO^-$ where the corresponding cation is H or a salt; $R_4$ is H; and $R_5$ is $NO_2$.

In another preferred embodiment, the present invention discloses a sialidase inhibitor wherein dashed lines $d_1$ and $d_2$ are both unsaturations, $X_1$ is NH; $R_1$ is $CH_3CO$; $R_2$ is OH; $R_6$ is H; $R_3$ is $COO^-$ where the corresponding cation is H or a salt; and $R_4$ is H; and $R_5$ is $CH(OH)CH_2NH_3^+$.

Another preferred embodiment of the present invention discloses a sialidase inhibitor wherein dashed lines $d_1$ and $d_2$ are both unsaturations, $X_1$ is NH; $R_1$ is $CH_3CO$; $R_2$ is OH; $R_6$ is H; $R_3$ is $COO^-$ where the corresponding cation is H or a salt; and $R_4$ is H; and $R_5$ is $CH(CH_2OH)CH_2NH_3^+$.

In yet another preferred embodiment, the present invention discloses a sialidase inhibitor wherein dashed lines $d_1$ and $d_2$ are both unsaturations, $X_1$ is NH; $R_1$ is $CH_3CO$; $R_2$ is OH; $R_6$ is H; $R_3$ is $COO^-$ where the corresponding cation is H or a salt; and $R_4$ is H; and $R_5$ is $CH(CH_2OHCH_2OH)CH_2NH_3^+$.

In another preferred embodiment, the present invention discloses a sialidase inhibitor wherein dashed lines $d_1$ and $d_2$ are both unsaturations, $X_1$ is NH; $R_1$ is $CH_3CO$; $R_2$ is OH; $R_6$ is H; $R_3$ is $COO^-$ where the corresponding cation is H or a salt; and $R_4$ is C; and $R_5$ is N, and $R_4$ forms a 5-membered ring with $R_5$ and $R_4$ is substituted with OH, $R_5$ is substituted with $CH_2NH_3^+$ and the intermediate carbon between $R_4$ and $R_5$ is substituted with OH, and where the 5-membered ring is unsaturated.

In yet a further preferred embodiment, the present invention discloses a sialidase inhibitor wherein dashed lines $d_1$ and $d_2$ are both unsaturations, $X_1$ is NH; $R_1$ is $CH_3CO$; $R_2$ is OH; $R_6$ is H; $R_3$ is $COO^-$ where the corresponding cation is H or a salt; and $R_4$ is C; and $R_5$ is N, and $R_4$ forms a 5-membered ring with $R_5$ and $R_4$ is unsubstituted, $R_5$ is substituted with $CH_2NH_3^+$ and the intermediate carbon between $R_4$ and $R_5$ is substituted with OH, and where the 5-membered ring is unsaturated.

In yet another preferred embodiment, the present invention discloses a sialidase inhibitor wherein dashed lines $d_1$ and $d_2$ are both unsaturations, $X_1$ is NH; $R_1$ is $CH_3CO$; $R_2$ is OH; $R_6$ is H; $R_3$ is $COO^-$ where the corresponding cation is H or a salt; and $R_4$ is C; and $R_5$ is N, and $R_4$ forms a 5-membered ring with $R_5$ and $R_4$ is unsubstituted, $R_5$ is substituted with $CH_2NH_3^+$ and the intermediate carbon between $R_4$ and $R_5$ is substituted with $CH_2(CH_2OH)_2$, and where the 5-membered ring is unsaturated.

In another preferred embodiment, the present invention discloses a sialidase inhibitor wherein dashed lines $d_1$ and $d_2$ are both unsaturations, $X_1$ is NH; $R_1$ is $CH_3CO$; $R_2$ is OH; $R_6$ is H; $R_3$ is $COO^-$ where the corresponding cation is H or a salt; and $R_4$ is C; and $R_5$ is N, and $R_4$ forms a 5-membered ring with $R_5$ and $R_4$ is unsubstituted, $R_5$ is substituted with $CH_2NH_3^+$ and the intermediate carbon between $R_4$ and $R_5$ is substituted with $C(CH_2OH)_3$, and where the 5-membered ring is unsaturated.

Another preferred embodiment of the present invention discloses a sialidase inhibitor wherein dashed lines $d_1$ and $d_2$ are both unsaturations, $X_1$ is NH; $R_1$ is $CH_3CO$; $R_2$ is OH; $R_6$ is H; $R_3$ is $COO^-$ where the corresponding cation is H or a salt; and $R_4$ is C; and $R_5$ is N, and $R_4$ forms a 5-membered ring with $R_5$ and $R_4$ is unsubstituted, $R_5$ is substituted with $CH_2CH_2NH_3^+$ and the intermediate carbon between $R_4$ and $R_5$ is substituted with OH, and where the 5-membered ring is unsaturated.

The present invention also discloses pharmaceutical compositions for inhibiting sialidase, comprising an inhibiting effective mount of a compounds of the invention and a pharmaceutically acceptable carrier.

In yet another preferred embodiment, the present invention discloses a method of inhibiting sialidase, comprising administering to a subject an inhibiting effective mount of a compound of the invention.

In a further preferred embodiment, the present invention presents a method of making a composition for inhibiting sialidase, comprising admixing an inhibiting effective amount a compound of the invention with a pharmaceutically acceptable carrier.

In yet another preferred embodiment, the present invention discloses a method of preventing bacterial or trypanosomal infection, comprising administering to a subject preventative effective amount a compound of the present invention.

Finally, the present invention discloses, in yet another preferred embodiment, a method of treating bacterial or trypanosomal infection, comprising administering to a subject treatment effective amount a compound of the invention.

A. Structure-Based Solutions

Structure-based drug design developed out of the fact that potential drugs had previously been discovered only serendipitously or by the use of extensive screening assays. To improve the therapeutic properties of existing compounds, traditional methods such as qualitative structure-activity relationship (QSAR) analysis have been used. However, to clearly understand the multitude of forces which affect a drug's biological activity (or lack thereof), the three-dimensional structure of the native target, or more preferably, the complex between the target and the drug, must be solved. In many cases, the structure of a particular drug-target complex can provide an immediate explanation to long-standing and perplexing biochemical questions of function and activity. Hence, the method of structure-based drug design, which uses the three-dimensional structure of a selected target or target-drug complex to guide the design new compounds. By starting with the structure of the target, the structure-based drug design protocol circumvents the problems and limitations associated with traditional methods of drug development. New compounds that show high specificity and affinity for the target site can be developed using the chemical and geometric structure of target site at high resolution and structure-based design [Ealick, S. E., Babu, Y. S., Bugg, C. E., Erion, M. D., Guida, W. C., Montgomery, J. A. & Secrist III, J. A. (1991). Application of crystallographic and modeling methods in the design of purine nucleoside phosphorylase inhibitors. *Proceedings of the National Academy of Science, USA* 88, 11540–441 ].

As recently as 1987, to develop a marketable new drug by traditional methods cost an estimated $231 million and required 12 years. The enormous number of potential compounds that are chemically synthesized contributes to the high cost of traditional development methods. Also, traditional methods are inefficient because many synthesized compounds are eventually rejected due to poor activity or adverse side effects. In comparison, the time requirement and costs of developing a drug using structure-based design methods are much lower. In this newer approach, the candidate drugs are modeled into the three-dimensional structure of the target before synthesis and only sterically and chemically compatible structures are synthesized. The screening process further increases the likelihood that the candidate compounds will bind to the active site. The current invention targets bacterial sialidase.

B. Structure-Based Design of Anti-Bacterial and Anti-Trypanosomal Compounds

Bacterial sialidases have been implicated and correlated with several disease such as, inter alia, dental caries, bacterial vaginosis, middle ear effusions, arteritis, acne, and acute streptococcal infection. Though many antibiotics are available to treat bacterial infections, they are often expensive or have significant side effects for the subject. The bactericidal agents of the present invention, however, do not suffer from the expense or potential side effects. Also, basic scientific research into the role of sialidases in bacterial biology and infection would benefit from the elucidation of bacterial-specific sialidase inhibitors.

In addition to bacteria, there are unique enzymes found only in trypanosomes which are also ideal targets for developing anti-trypanosomal therapeutics. One trypanosomal target is the cell-surface anchored trans-sialidase enzyme, which transfers a terminal sialic acid from a donor sialoglycoconjugate to a terminal β-1,4-linked galactose acceptor. The trans-sialidase enzyme found in the protozoa Trypanosomatidae family is believed to play a important role in several human diseases, such as Chagas' disease (*Trypanosoma cruzi*) and African sleeping disease (*Trypanosoma gambiense* and *T. rhodesiense*), as well as, in several animal trypanosomiasis (*Trypanosoma brucei*, and potentially *T. evansi*, *T. congolense*, and *T. vivax*). It is estimated that there are several million cases of Chagas' disease in Central and South America, as well as several millions cases of African sleeping sickness in sub-Sahara Africa. Every year, several thousand new cases of Chagas' disease and African sleeping sickness occur. The rate of trypanosomiasis in the animal kingdom, which can have serious health and economic implications, is difficult to quantify but is potentially several million cases. Though previous drugs have been developed to treat the trypanosomal infections in humans and animals, they are either relatively toxic to the host or the target trypanosome strains have developed a drug resistance mechanism. Inhibitors of trans-sialidase promise to be effective anti-trypanosomal agents because the trypanosomal trans-sialidase enzyme has been shown to be required for infection in humans, as well as, in animals (limited data) [de Titto, E. H. & Araujo, F. G. (1987). Mechanism of cell invasion by Trypanosoma cruzi: importance of sialidase activity. Acta Trop. (Basel), 44, pp. 273–82; Ming, M., Chuenkova, M., Ortega-Barria, E. & Pereira, M. E. (1993). Mediation of Trypanosoma cruzi invasion by sialic acid on the host cell and trans-sialidase on the trypanosome. *Mol Biochem Parasitol.*, 59, pp. 243–52; and Prioli, R. P., Mejia, J. S. & Peteira, M. E. (1991). On the interaction of Trypanosoma cruzi neuraminidase and human lipoproteins. *Eur J Epidemiol.*, 7, pp. 344–8]. The structure-based design of the present invention has led to specific drugs for the trans-sialidase active site. Based on those structures, the drugs of the present invention have a reduced possibility of harming the host or eliciting a drug resistance due to mutation of the target site.

C. *Salmonella typhimurium* Sialidase Activity

The sialidase gene, nanH, from the enteric Gram-negative bacterium *S. typhimurium* has been cloned and the expressed bacterial sialidase has been well characterized [Hoyer, L. L., Roggentin, P., Schauer, R. & Vimr, E. R. (1991). Purification and properties of cloned Salmonella typhimurium LT2 sialidase with virus-typical kinetic preference for sialyl alpha 2→3 linkages. *J Biochem.*, 110, pp. 462–7; Hoyer, L. L., Hamilton, A. C., Steenbergen, S. M. & Vimr, E. R. (1992). Cloning, sequencing and distribution of the Salmonella typhimurium LT2 sialidase gene, nanH, provides evidence for interspecies gene transfer. *Molecular Microbiology* 6(7), 873–84]. No significant differences were detected in the expressed enzyme as compared to the wild type sialidase, except in the wild type strain, the sialidase accounts for <1% of the total protein. The *S. typhimurium* sialidase has a 260-fold cleavage preference for $\alpha2\rightarrow3$ over $\alpha2\rightarrow6$ linked sialic acids. In addition, the *S. typhimurium* sialidase has a high enzymatic activity for ganglioside and mucin substrates containing terminal sialic acids. The *S. typhimurium* sialidase does not efficiently recognize $\alpha2\rightarrow8$ or $\alpha2\rightarrow9$ linked sialic acids and therefore shows little cleavage activity for colominic acid, which is a homopolymer of sialic acid, or Group C polysaccharides.

Like the influenza virus sialidase, the *S. typhimurium* sialidase is active over a broad pH range of pH 5.5–7.0, but unlike viral sialidase, the bacterial sialidase does not require divalent metal ions for activity. Using 4-methylumbelliferyl-a-D-N-acetylneuraminic acid (MUN) as the substrate, the *S. typhimurium* sialidase displays a $K_m=2.5\times10^{-4}$M, and a turnover number $=2,700$ sec$^{-1}$. The dehydro analog of sialic acid, Neu5Ac2en, inhibits *S. typhimurium* sialidase with a $K_i=0.38$ mM. As compared to influenza virus sialidase, high levels of the cleavage product, Neu5Ac, do not inhibit the bacterial sialidase.

D. *Salmonella typhimurium* Sialidase Structure

The *S. typhimurium* sialidase has a molecular weight of 41 kDa and a pI>9. As stated above, the three-dimensional structure of *S. typhimurium* was determined using x-ray crystallography [Crennell et al., 1993]. The structure was solved to 2.0Å by the multiple isomorphic replacement method and refined to a crystallographic R-factor of 18.9%. Like influenza virus sialidase, the *S. typhimurium* sialidase is folded into a left-handed propeller motif consisting of six, four-stranded antiparallel β-sheets. The length of the β-strands and the loops connecting the β-strands differs markedly from the viral sialidase structure. One disulfide bond is observed in the *S. typhimurium* sialidase which links the first and second β-sheets.

E. Trypanosomal Trans-sialidase

The atomic structure of the N-terminal trans-sialidase domain of the trypanosomal trans-sialidase protein has not been solved. But the trypanosomal trans-sialidase N-terminal domain has a high sequence homology to the *S. typhimurium* sialidase [Pereira, M. E., Mejia, J. S., Ortega-Barria, E., Matzilevich, D. & Prioli, R. P. (1991). The Trypanosoma cruzi neuraminidase contains sequences similar to bacterial neuraminidases, YWTD repeats of the low density lipoprotein receptor, and type III modules of fibronectin. *J Exp Med*, 174, pp. 179–91 ]. Using the sequence alignment of the trypanosomal trans-sialidase to the bacterial sialidase and using the *S. typhimurium* sialidase crystal structure, a three-dimensional model of the trans-sialidase active site was constructed.

The amino acid sequence for trans-sialidase determined by Pereira et al ( 1991 ) was compared to the sialidases isolated from the bacteria *Clostridium perfringens* and *Salmonella typhimurium*. The GCG package [Program Manual for the Wisconsin Package, Version 8, September 1994, Genetics Computer Group, Madison, Wis.] of alignment programs was used to align the three sialidase sequences. The protein database entries used were styneur. pep (*S. typhimurium* ) and cfsiali.pep (*C. perfringens*). The inclusion of other bacterial sialidase sequences in addition to the Salmonella and Clostridium sequences did not improve the overall fit of the of the bacterial enzymes to the trans-sialidase. The major features of the proposed bacterial sialidase-trypanosomal trans-sialidase sequence alignment are as follows.

First, the sequence alignment did not predict a trans-sialidase partner for Arg 37 in *S. typhimurium* sialidase sequence. This arginine is part of the arginine triad found in all influenza and bacterial sialidases to date and is required to bind the carboxylate group of the substrate, sialic acid. Second, three cysteine residues in the bacterial sialidase are replaced by non-cysteine residues in the predicted trans-sialidase alignment. The three residues affected are Cys 103, Cys 225, and Cys 344 (*S. typhimurium* numbering). Third, two non-cysteine residues in the bacterial sialidase are predicted to be cysteine residues in the trypanosomal trans-sialidase. The residues in *S. typhimurium* which change to cysteines in the trans-sialidase are Lys 94 and Gly 229. Note, neither the Lys or Gly residues are conserved in the *C. perfringens sialidase*.

On the basis of the proposed sequence alignment, the active site residues of the Salmonella structure were replaced with the trans-sialidase residues identified from the sequence alignment. The program SAM in the FRODO package was used the construct the trans-sialidase homology model. SAM builds the new residues using the original residue atom positions of the *S. typhimurium* crystal structure. One round of limited energy minimization was applied to the trans-sialidase homology model.

F. In Vitro Testing of Benzoic Acid Inhibitors Against Bacterial Sialidase

Aside from moderate inhibitory activity, carbohydrate based inhibitors of sialidase such as Neu5Ac2en suffer as potential therapeutics due to the unfavorable economics and difficulty of manufacturing large scale amounts of the compounds. Benzoic acid based sialidase inhibitors are chemically easier and cheaper to synthesize.

In addition, there are numerous common synthetic routes available to selectively modify a benzene ring with different chemical functional groups. Furthermore, substitution of a benzene ring for the sugar ring of Neu5Ac2en does not dramatically affect inhibitory activity. Previous studies have shown that the sugar ring of the carbohydrate-based inhibitors does not interact directly with the protein active site and only serves as a scaffolding to direct the placement of the inhibitor function groups. The similar geometry and size of a benzene ring to the carbohydrate ring of Neu5Ac2en supports the hypothesis that a benzene ring could act as a scaffolding element for inhibitor functional groups and, therefore, benzoic acid based compounds could inhibit sialidase activity.

Two benzoic acid derivatives, 4-acetylamino-3-hydroxyl-5-nitro-benzoic acid (HNBA) and 4-acetylamino-3-guanidino-benzoic acid (GBA), which are, respectively, millimolar and micromolar inhibitors of influenza virus sialidase, were tested for inhibitory activity against bacterial sialidase (*Micromonospora viridifaciens*) using a fluorescence assay and the substrate 4-methylumbelliferyl-a-D-N-acetylneuraminic acid (MUN). FIG. 1 shows the relative inhibition activity for the compounds HNBA and GBA versus Neu5Ac2en (bacterial sialidase $K_i\times10^{-6}$M) determined for *M. viridifaciens* bacterial sialidase.

The inhibition activities were determined using a modified standard fluorometric assay employing 4-methylumbelliferyl-a-D-N-acetylneuraminic acid (MUN) as the substrate. Since the benzoic acid compounds have a low solubility in water, a 100 mM stock solution of the benzoic acid compounds was prepared in the organic solvent dimethyl sulfoxide (DMSO). An appropriate amount of the DMSO stock solution was added to the reaction mixture which contained a final concentration of 10 mM inhibitor, 0.1 mM MUN, 50 mM NaAc (pH 6.0), 0.075 mM CaCl$_2$, 0.240 mM MgCl$_2$, 0.045 mM NaCl, and bacterial sialidase (diluted to give a linear response range in the fluorometer). Following addition of MUN, the sample was incubated at 37° C. for 15 minutes. The reaction was stopped by the addition of 25 mM HEPES (pH 11.0). The amount of fluorescent product generated in the reaction was measured using an excitement wavelength of 365 nm and emission wavelength of 450 nm.

The inhibition activity of Neu5Ac2en was standardized against a background control containing only water and no Neu5Ac2en. Likewise, the inhibition activity of the benzoic acid compounds was standardized against a control containing only DMSO to negate the potential inhibition effects of DMSO on bacterial sialidase. Due to standardization, the inhibition activities of Neu5Ac2en and the benzoic acid inhibitors are reported as percent inhibition values. The percent inhibition of Neu5Ac2en serves as a positive control for inhibition by the benzoic acid compounds.

G. Modeling of Inhibitors into Bacterial Sialidase

The compounds, HNBA and GBA, are potent inhibitors of both type A and B influenza virus sialidase. The $IC_{50}$ for HNBA inhibition of influenza virus sialidase is approximately 10 mM, similar to the Neu5Ac2en $IC_{50}$ for influenza virus sialidase inhibition. Based on the inhibition assay results, HNBA and GBA also inhibited bacterial sialidase with efficiencies similar to Neu5Ac2en.

Initial modeling of the benzoic acid lead compounds into the bacterial sialidase was guided by the crystal structure of the Neu5Ac2en-bacterial sialidase complex. The placement of the benzoic acid inhibitors into the bacterial active site by superposition onto the Neu5Ac2en position did not disturb the overall geometry of the active site, as evidenced by the low root-mean-square deviation between the energy minimized benzoic acid and Neu5Ac2en bacterial sialidase complexes.

In the bacterial sialidase, superposition of GBA to align its guanidinium group to the Neu5Ac2en O4 hydroxyl group, which will mimic the 4-guanidino-Neu5Ac2en binding mode, is not possible due to steric conflicts with residues Arg 56 and Asp 100 in bacterial sialidase. This steric interference in the Neu5Ac2en O4 pocket also explains the inhibition selectivity of 4-guanidino-Neu5Ac2en for influenza virus sialidase versus bacterial sialidases. The rotation of the GBA ring resulting from energy minimization may be due to the lack of an hydroxyl group at the C5 position in GBA, which would bind in the Neu5Ac2en O4 hydroxyl site.

H. Modeling and GRID Analysis of Inhibitor-Bacterial Sialidase Complexes

Figure 2A:
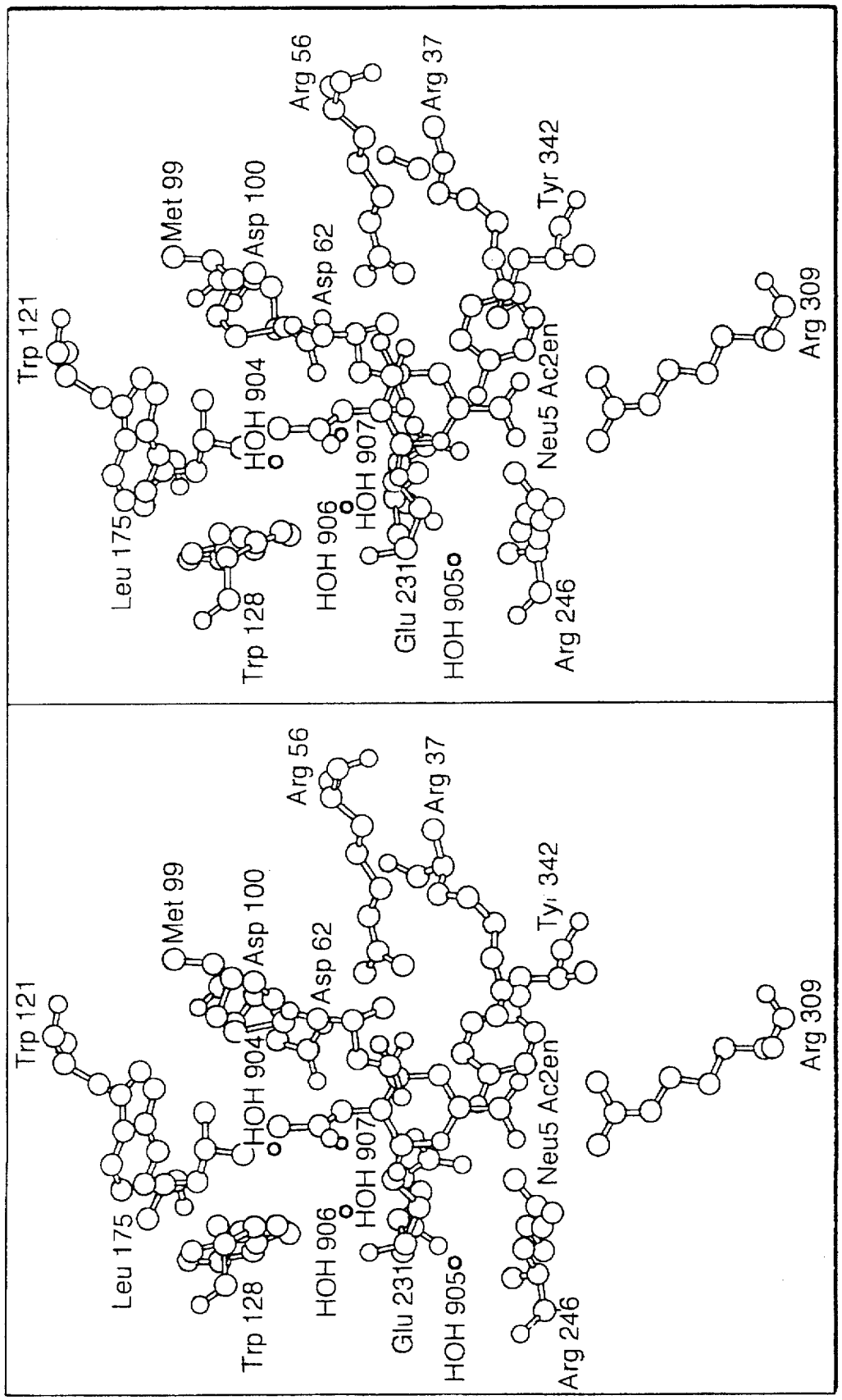
FIG. 2a shows a stereopair view of energy minimized Neu5Ac2en in the sialidase binding site.

The structure of a prototypical bacterial sialidase from *S. typhimurium* complexed with the inhibitor Neu5Ac2en by Crennell et al. was used to position the benzoic acid inhibitors HNBA and GBA into the bacterial sialidase active site. The interactions between Neu5Ac2en and the active site of the bacterial sialidase are shown in FIG. 2a.

Figure 3A:
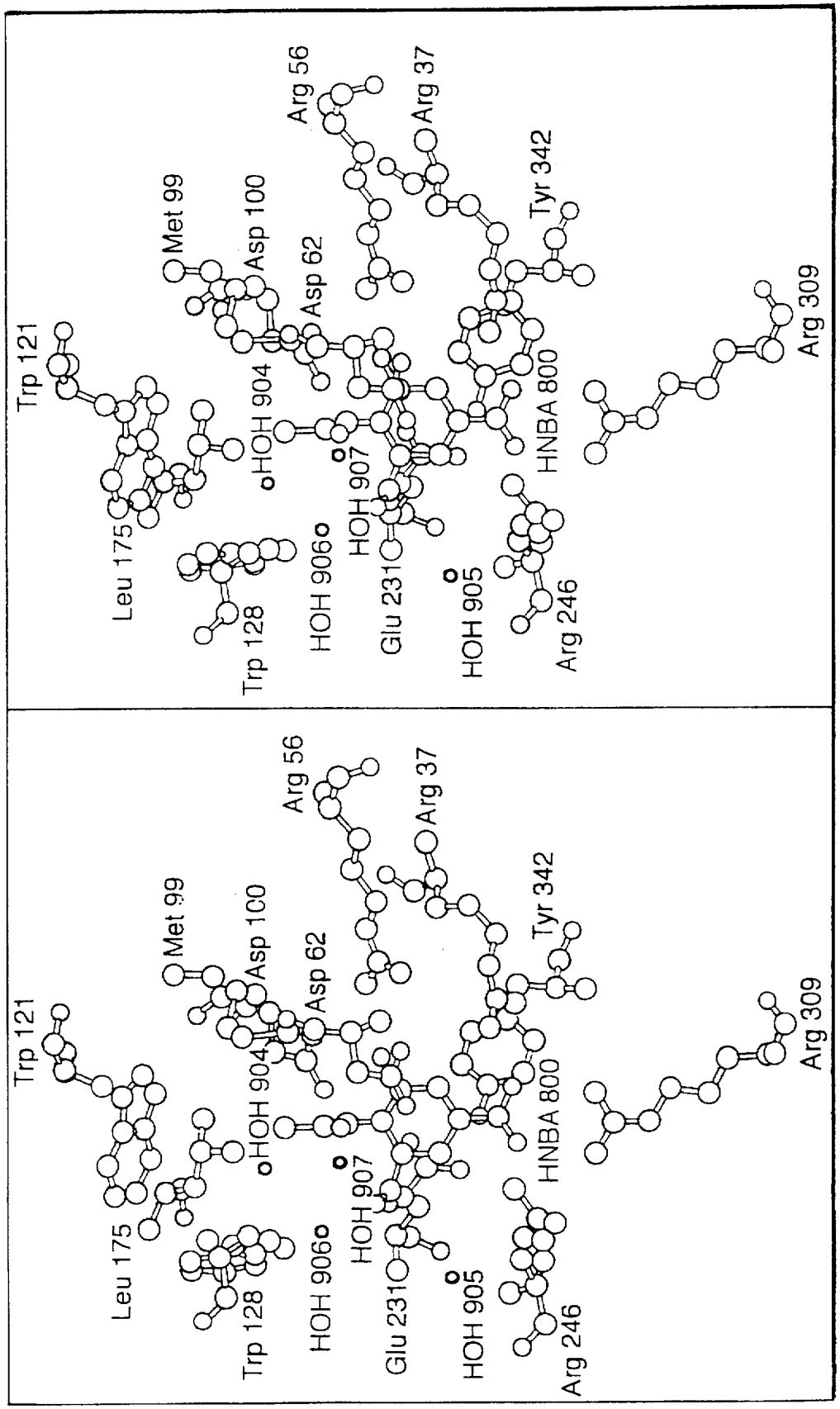
FIG. 3a shows a stereopair view of energy minimized HNBA in the sialidase binding site.

To model the HNBA-bacterial sialidase complex, the C1, O3, and C5 atoms of HNBA were superimposed onto the C2, O4, C6 atoms of Neu5Ac2en using a least-squares approach. The superposition aligns the C1 carboxylate, C3 hydroxyl, and C4 acetylamino groups of HNBA with the C2 carboxylate, O4 hydroxyl, and C5 acetylamino groups of Neu5Ac2en and preserves the important interactions of these groups with the bacterial sialidase active site residues in the HNBA-bacterial sialidase modeled complex. See FIG. 3a.

Figure 3B:
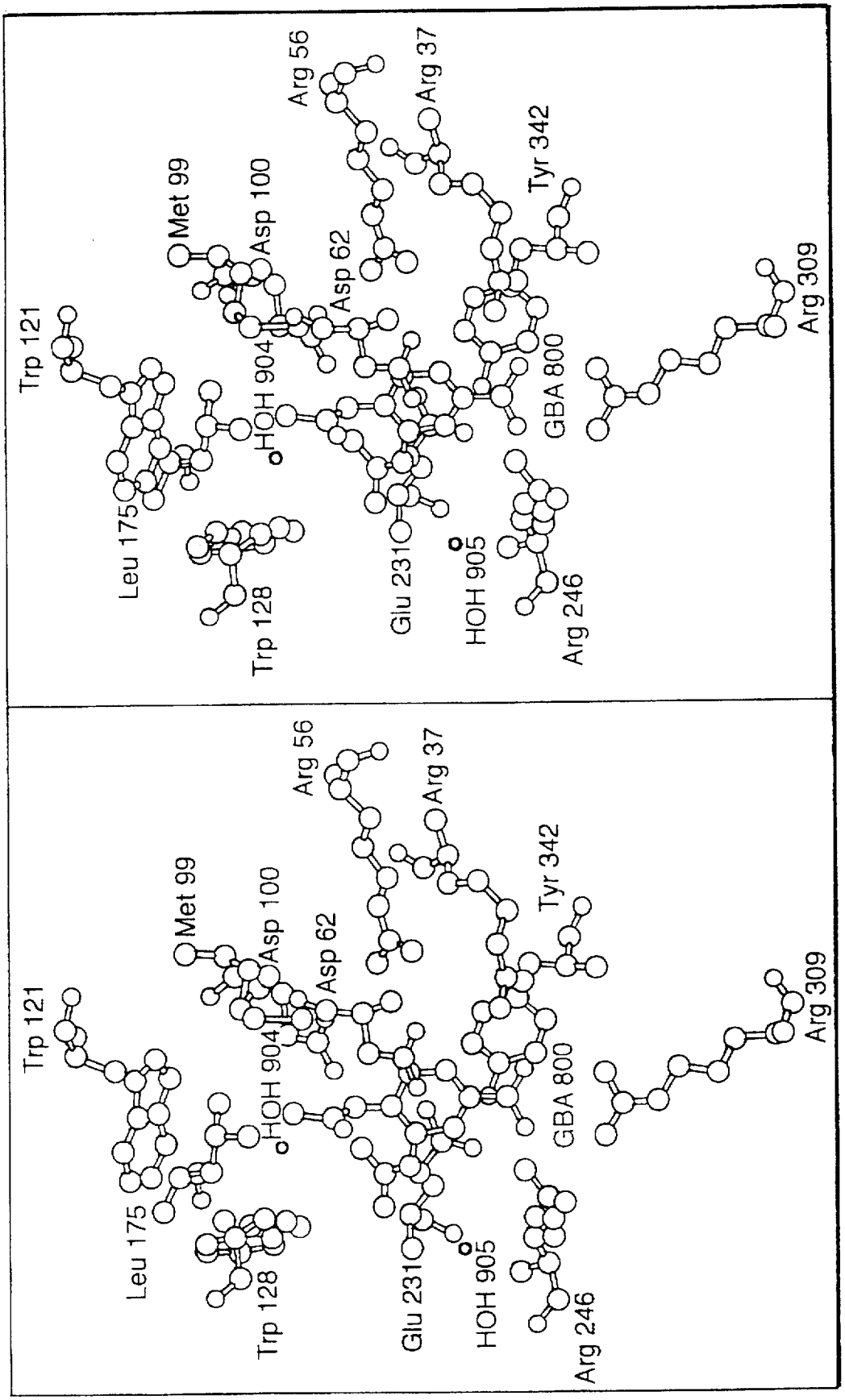
FIG. 3b shows a stereopair view of energy minimized GBA in the sialidase binding site.

The GBA-bacterial sialidase complex was modeled by a least squares superposition of the C1, N3, and C5 atoms of GBA onto the C2, C7, and C3 atoms of Neu5Ac2en. See FIG. 3b. The superposition aligns the GBA guanidinium group to the Neu5Ac2en glycerol group in the bacterial sialidase active site. This orientation corresponds to the binding mode observed in the GBA influenza virus type A N2 sialidase complex. Following the initial least squares superposition, the guanidinium sidegroup of GBA was manually rotated into the $N3^+$ binding site A identified in the GRID map analysis on a graphics display using the program FRODO.

All of the water molecules identified in the Neu5Ac2en-bacterial sialidase crystal structure were included in the HNBA-bacterial sialidase model. The criteria for retaining the waters in the HNBA-bacterial sialidase complex was that none of the water molecules were sterically excluded by the presence of the HNBA inhibitor and all of the water molecules possessed potential hydrogen bonding partners. In the GBA-bacterial sialidase, two of the water molecules in the Neu5Ac2en-bacterial complex, HOH 906 and HOH 907, were excluded due to steric overlap with the GBA guanidino group.

The HNBA and GBA bacterial sialidase complexes were energy minimized using a conjugate gradient protocol within the program X-PLOR to relieve steric conflicts that may have resulted from the Neu5Ac2en superposition. A harmonic constraint of 500 kcal/mol was placed on atoms more than 10Å distant from the benzoic acid compound, while those atoms within a 10 Å radius of the benzoic acid compound had no harmonic constraints. The active site geometry in the energy minimized benzoic acid-bacterial sialidase complexes was almost identical to that observed in the energy minimized Neu5Ac2en-bacterial sialidase complex. Energy minimization of the HNBA-bacterial sialidase complex did not significantly alter the orientation of HNBA in the bacterial sialidase active site. Surprisingly, energy minimization of the GBA-bacterial sialidase complex changed the orientation of GBA in the bacterial sialidase active site when compared to the starting position (Neu5Ac2en least squares superposition). In the energy minimized GBA-bacterial sialidase complex, the benzene ring of GBA is rotated approximately 20° around the inhibitor carboxylate-acetylamino axis. The rotation places the GBA guanidino group closer to the $N3^+$ binding site and tilts the benzene ring C5 and C6 atoms away from the active site floor. Despite the tilt in the GBA benzene ring, no change in orientation was observed for the GBA carboxylate and N-acetylamino groups in the energy minimized GBA-bacterial sialidase complex when compared to the energy minimized HNBA-bacterial sialidase complex. In addition, the active site residues in both of the energy minimized benzoic acid-bacterial sialidase complexes adopt conformations which are analogous to the active site residues of the energy minimized Neu5Ac2en-bacterial sialidase. The root-mean-square (rms) deviation for sialidase atoms within the 10 Å radius between the energy minimized Neu5Ac2en and HNBA-bacterial sialidase complexes, is 0.05 Å, between the minimized Neu5Ac2en and GBA-bacterial sialidase complexes, 0.07 Å.

GRID maps were calculated to identify favorable probe binding sites in the *S. typhimurium* bacterial sialidase active site for the purpose of improving the activity of the lead compounds. GRID determines the interaction energy between a given probe and a protein target site as the probe is placed at each point within a three-dimensional lattice centered at the target site. By displaying GRID maps contoured at specific interaction energies on a graphics system, potential binding sites for the selected probes were identified. Probe functionalities which display favorable interaction energies were then be incorporated into the lead compound to create new ligands with potentially higher affinities for the target site.

The GRID calculations were performed using the HNBA-bacterial sialidase complex modified by the deletion of the C5 nitro group coordinates (i.e. 4-acetylamino-3-hydroxylbenzoic acid=HBA). Removal of the C5 nitro group allows a larger region of the active site be included in the GRID search. Two sets of GRID maps were calculated using the coordinates of the HBA-bacterial sialidase complex: i) either in the presence of waters or ii) in the total absence of waters.

Five probe types were selected for the GRID calculations: a) C3 (—CH$_3$), a hydrophobic probe; b) N3$^+$ (NH$_3^+$), a cationic probe; c) F$^-$, an artionic probe; d) O═ (carboxylate C═O ), a polar hydrogen bond donor probe; and e) OH2 (water), a hydrogen bond donor/acceptor probe. No changes were made to the chemical default parameters for each probe type. The lattice used in our GRID calculations was defined as a box with edges roughly 10 Å greater the maximum dimensions of HNBA in the HNBA-bacterial sialidase complex. The GRID box size results in a GRID search step size of 0.126 Å along the x-axis, 0.117 Å along the y-axis, and 0.141 Å along the z-axis.

An internal calibration of favorable interaction energy levels was provided by the OH2 GRID map calculated for the HBA-bacterial sialidase complex model without waters. In this GRID map, the binding sites of several water molecules observed in the active site of the Neu5Ac2en-bacterial sialidase crystal structure were successfully predicted by the OH2 probe. Probe binding sites were considered significant if they had an interaction energy less than the average interaction energy exhibited by the crystallographic water molecules, i.e. energies less than approximately −5 kcal/mol.

For the first set of GRID calculations which used the HBA-bacterial sialidase coordinates in the absence of water molecules, only the N3$^+$ and OH2 probes produced maps that contained highly favorable probe binding sites in the active site. The GRID maps generated using the F$^-$ and O═ probes did not produce any significant probe binding sites in the active site region. The C3 GRID map gave a good indication of the accessible volume which preferred van der Waals interactions. These C3 sites had high interaction energies (greater than −2 kcal/mol) and were reproducible to a large extent with the remaining probes types. The hydrophobic binding pocket near Trp 128 which accommodates the hydrophobic C9 methyl group of Neu5Ac2en was the most prominent site defined by the C3 probe. Binding sites for the C3 probe were also found in the active site pocket responsible for binding the Neu5Ac2en glycerol group.

Figure 5:
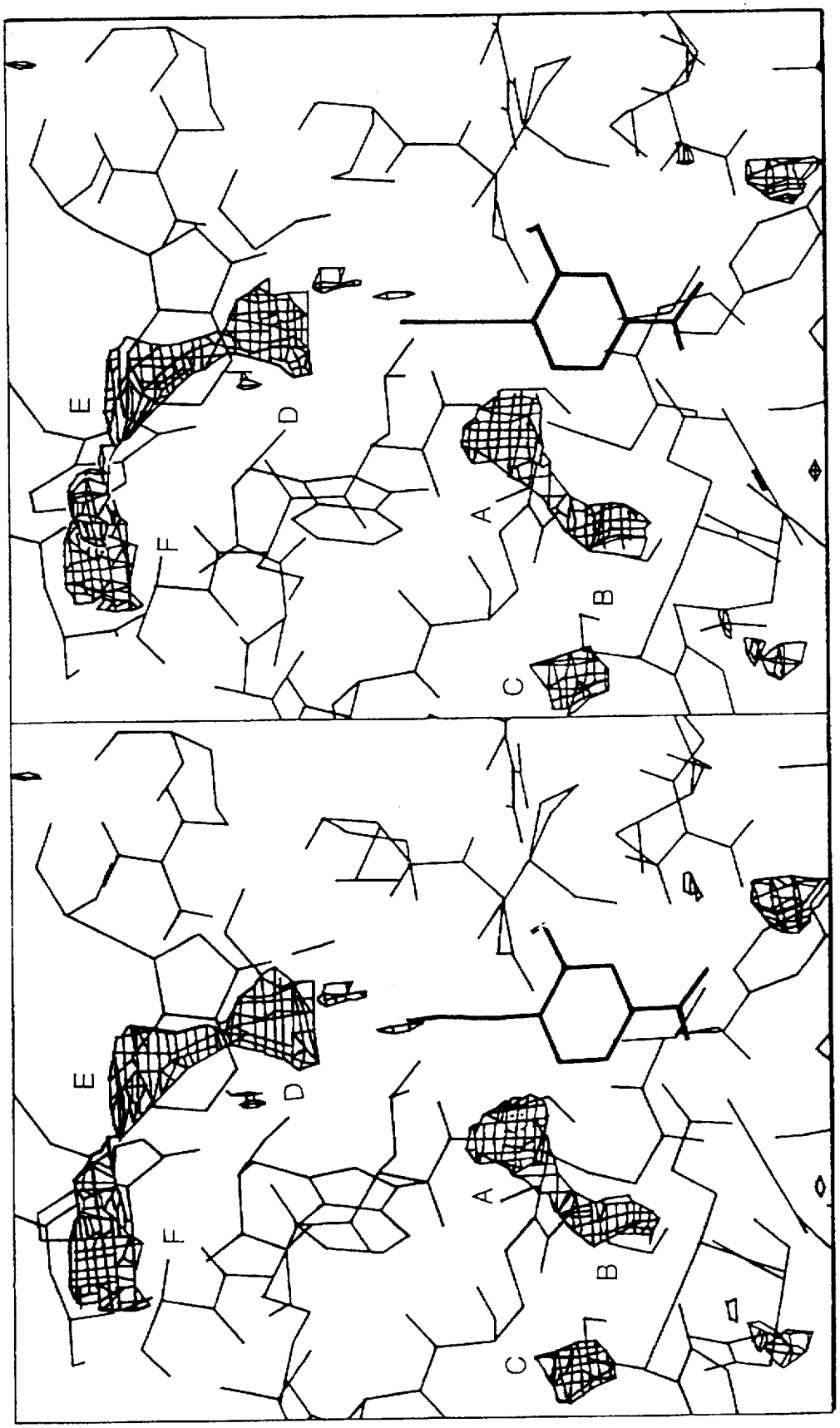
FIG. 5 shows a GRID map with 4-acetylamino-3-hydroxyl-benzoic acid (HBA) using an $N_3^-$ probe at -18 kcal/mol and an $OH_2$ probe at -6 kcal/mol. Binding sites A through F are also labelled.

The major feature of the N3$^+$ GRID map calculated using the HNBA-bacterial sialidase complex in the absence of the water molecules, was binding site A which overlapped the HOH 906 and HOH 907 binding sites (FIG. 5). This binding site favors a positive charge due to the presence of the neighboring acidic residues Asp 100 and Glu 231. Of all the GRID maps calculated using the five probe types, this site in the N3$^+$ map had the most significant interaction energy (−29 kcal/mol).

The OH2 GRID map calculated using the HBA-bacterial sialidase complex coordinates in the absence of the water molecules was used to predict several areas within the active site which should favor hydrogen bonding. The first favorable binding site for a water probe is site A, which is also the highly favorable N3$^+$ probe binding site. The second water probe binding site is B which slightly overlaps site A. Site A and B roughly correspond to the binding sites of HOH 906 and HOH 907 and both sites have a maximum water probe interaction energy of approximately −7.5 kcal/mol. A third favorable site for OH2 binding in the glycerol active site pocket is site C. Site C does not correspond to any crystallographic water binding site and has a maximum interaction energy of approximately −9 kcal/mol. Finally, using the OH2 probe, the three discrete binding sites D, E and F were observed which form a long hydration channel in the active site. Binding site D corresponds to the position of HOH 904 and has a maximum interaction energy of −9 kcal/mol. The more distal binding sites E and F have maximum interaction energies of −10 and −9 kcal/mol and do not contain any crystallographically determined water binding sites.

The coordinates of the HBA-bacterial sialidase complex in the presence of the water molecules were used to calculate a second set of GRID maps utilizing the C3, N3$^+$, F$^-$, O═, and OH2 probe types. No new probe binding sites in the sialidase active site were identified for the second set of GRID maps which were not present in the first set of GRID maps calculated in the absence of water residues.

I. Construction of New Inhibitors Specific for Bacterial Sialidase

A new series of novel compounds (INSA series) were composed which take advantage of the favorable binding sites predicted from the GRID map analysis, while still retaining the favorable inhibitor-protein interactions of the C1 carboxylate, C3 hydroxyl and C4 acetylamino groups. Using the HNBA-bacterial sialidase coordinates as a template, the new compounds were constructed on a graphics display running the program FRODO. Three subclasses of novel, potential bacterial sialidase inhibitors were composed as preferred embodiments and designated as INSA class I, II, and III. These classes are subgenera of the invention genus set forth in General Structure I:

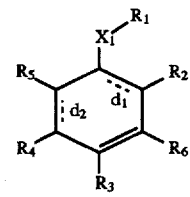

General Structure (I)

wherein the dashed lines d$_1$ and d$_2$ are independently unsaturations or saturations and the core ring is cyclic or heterocyclic with one to two heteroatoms of O, N, or S; X$_1$ is CO, SO$_2$, NH, CH$_2$, S, or O; R$_1$ is NH$_2$, SH, OCH$_3$, halide, COA$_1$, where A$_1$ is branched or unbranched, alkyl, alkenyl or alkynyl of from 1 to 5 carbons, and A$_1$ is unsubstituted or substituted independently with one or more substitutions of OH, SH, NH$_2$ or halide, a branched or unbranched, alkyl, alkenyl or alkynyl of from 1 to 6 carbons, unsubstituted or substituted independently with one or more substitutions of OH, SH, NH$_2$ or halide, or a 5-, 6-, or 7-membered first ring, saturated or unsaturated, unsubstituted or substituted independently with one or more substitutions of (a) OH or (b) a branched or unbranched, alkyl, alkenyl or alkynyl of from 1 to 6 carbons, unsubstituted or substituted independently with one or more substitutions of OH, SH, NH$_2$ or halide, where the 5-, 6-, or 7-membered first ring is cyclic or heterocyclic with one to two heteroatoms of O, N, or S; R$_2$ and R$_6$ are independently H, OH, SH, NH$_2$, halide, or A$_2$ where A$_2$ is alkyl, alkoxy, alkenyl, alkenoxy, alkynyl, or alkynoxy, or alkanol, alkenol, or alkynol of one or more OH moieties on the alkanol, alkenol, or alkynol, where A$_2$ is unbranched or branched, of from 1 to 4 carbons, and A$_2$ is unsubstituted or substituted independently with one or more substitutions of NH$_2$, COOH, halide, SH, OH, or guanidinium; R$_3$ is COO$^-$, POO$^-$, BOO$^-$ or SOO$^-$ where the corresponding cation is H or a salt; and wherein A) R$_4$ is H and R$_5$ is NO$_2$; B) R$_4$ is H, OH, SH, halide, COOH, guanidinium, or alkanol of one or more OH moieties, branched or unbranched, of from 1 to 4 carbons, and R$_5$ is A$_3$ where A$_3$ is alkyl, alkoxy, alkenyl, alkenoxy, alkynyl, or alkynoxy, or alkanol, alkenol, or alkynol of one or more OH moieties on the alkanol, alkenol, or alkynol, where A$_3$ is unbranched or branched, of from 1 to 4 carbons, and A$_3$ is unsubstituted or substituted independently with one or more substitutions of NH$_2$, COOH, halide, SH, OH, or guanidinium; or C) R$_4$ is C, CH or CH$_2$ and $R_5$ is CH or $CH_2$, and $R_4$ forms a 4-, 5-, or 6-membered second ring with $R_5$, where the second ring is saturated, partially unsaturated or fully unsaturated, cyclic or heterocyclic with one to two heteroatoms of O, N, or S substituted for any second ring carbon, and $R_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and $R_5$ is substituted with $A_4NH_3^-$, where $A_4$ is alkyl, alkenyl or alkynyl, or alkanol or alkenol of one or more OH moieties on the alkanol or alkenol, of from 1 to 3 carbons, and, for the 5- or 6-membered second ring, the intermediate second ring carbons between $R_4$ and $R_5$ are independently unsubstituted or substituted with one or more substitutions of OIL or alkanol, alkenol or alkynol of one or more OH moieties on the alkanol, alkenol, or alkynol, branched or unbranched, of from 1 to 4 carbons; or an analog, pharmaceutically acceptable salt, or derivative of the inhibitor of general structure I, with the proviso that when $X_1$ is NH $R_1$ is $COCH_3$, $R_2$ is OH, $R_6$ is H, and $R_3$ is $COO^-$, a) $R_5$ is not $NO_2$ or $NHC(NH)NH_2$ when $R_4$ is H and $d_1$ and $d_2$ are unsaturations and (b) $R_5$ is not $CH(OH)CH(OH)CH_2(OH)$ when $d_1$ and $d_2$ are saturations and the core ring is substituted with the heteroatom O at the core ring carbon adjacent to $R_4$.

As used herein, the term "salt" refers to the cation, such as $Li^-$, $K^+$, $Na^+$, $Ca^{2+}$, $Mg^{2+}$, $Al^{3+}$ etc., which corresponds to the $COO^-$, $BOO^-$, $POO^-$, or $SOO^-$ group of the inhibitors. Sodium salts are often preferable for pharmaceutical compositions. One of ordinary skill in the art would recognize that the fundamental utility of the compounds is not dependent upon the identity of the particular cation. As shown, $H^+$ is also a suitable cation.

In particular embodiments, the genus of structure I can be defined in three INSA subgenera. The class I compounds (INSA I-1, I-2, I-3, and I-4) were constructed to fill the mostly hydrophobic pocket formed by Trp 121, Trp 128 and Leu 175. Because of the lack of strong hydrogen bonds to the benzoic acid O8 atom, it was deemed feasible to cyclize the acetyl group into either a furan ring (compounds I-1, 1-2, and 1-3) or benzene ring (I-4) In the compounds I-1, I-2, and I-3, the furanyl- ring has a suitable size to fill the hydrophobic pocket and should pack favorably against the Trp 128 indole ring. To completely fill the hydrophobic pocket, methyl groups were added to the furanyl- ring of compounds I-2 and I-3. The C9 and the C10 position in compounds I-2 or I-3 were equally favored for methyl group addition. One of skill in the an would recognize that the hydrophobic pocket could be filled by any 5-, 6-, or 7-membered ring, saturated or unsaturated, unsubstituted or substituted with OH, $CH_3$ or glycerol, cyclic or heterocyclic with one or more heteroatoms of O, N, or S

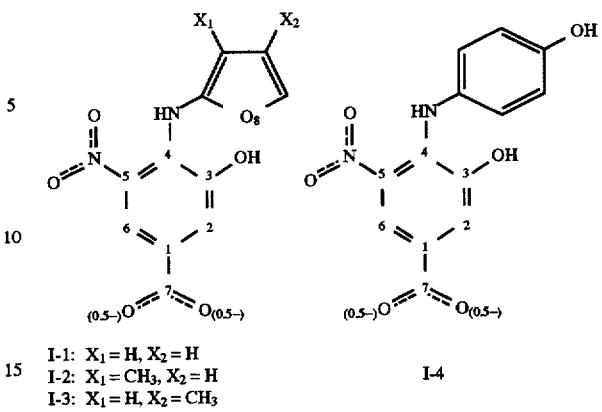

I-1: $X_1 = H, X_2 = H$
I-2: $X_1 = CH_3, X_2 = H$
I-3: $X_1 = H, X_2 = CH_3$

I-4

Figure 2B:
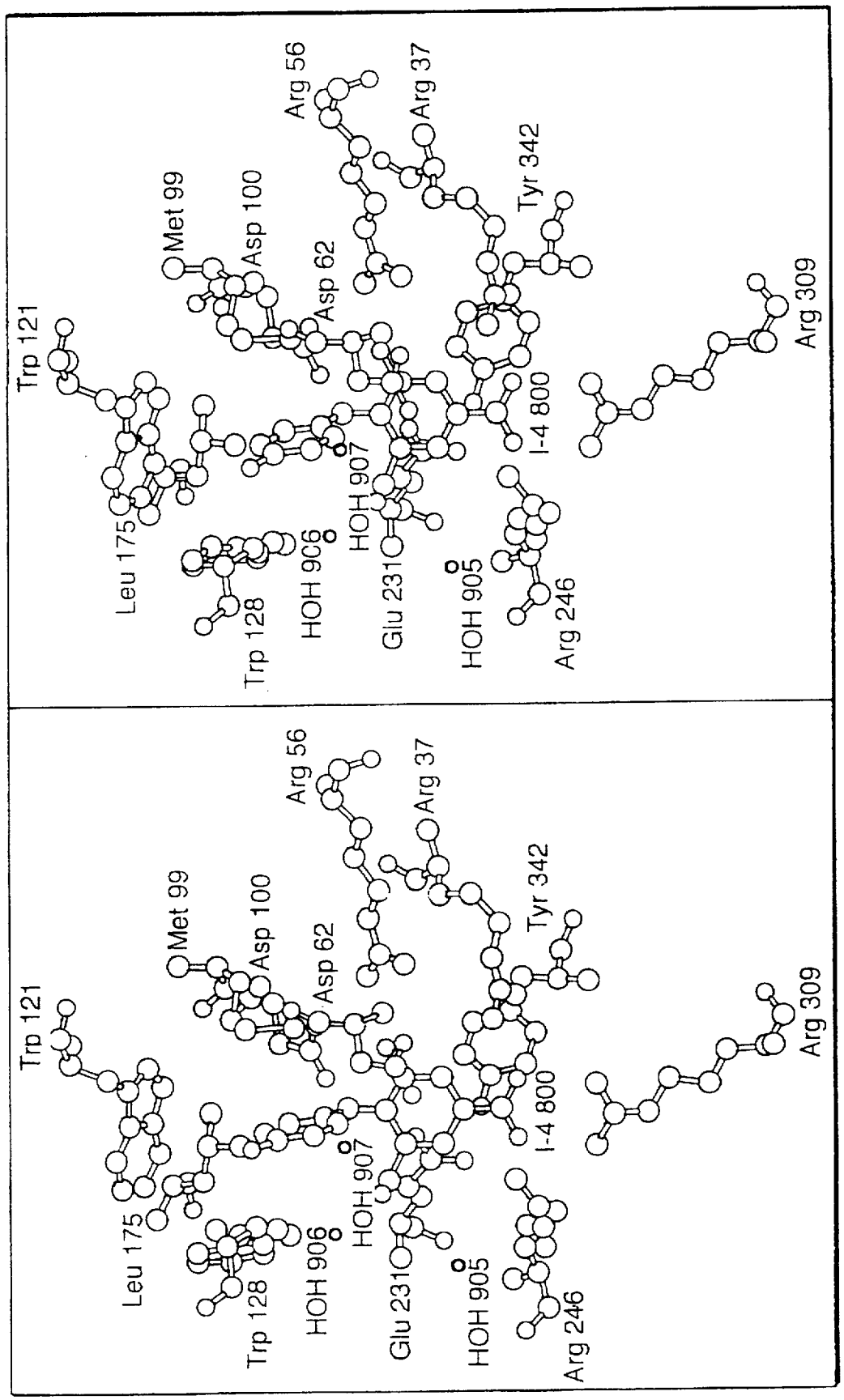
FIG. 2b shows a stereopair view of energy minimized INSA 1-I in the sialidase binding site.

The N-phenylamino group present in the I-4 compound has two favorable qualities First, the N-amino benzene ring of I-4, analogous to the other class I compounds, is good hydrophobic moiety and should fill the hydrophobic pocket formed by Trp 121, Trp 128, and Leu 175. Second, use of a N-amino benzene ring allows the placement of a hydroxyl group into site D, the favorable OH2 binding site determined from the GRID calculations Because the OH2 interaction energy for site D is significant, the addition of a phenyl hydroxyl group in site D should substantially contribute to the binding energy of compound I-4. See FIG. 2b The placement of a suitable hydrogen bond donor/acceptor moiety in pocket D in the INSA I-1, I-2, and I-3 compounds is not possible due to the geometry of the furan ring.

Figure 4A:
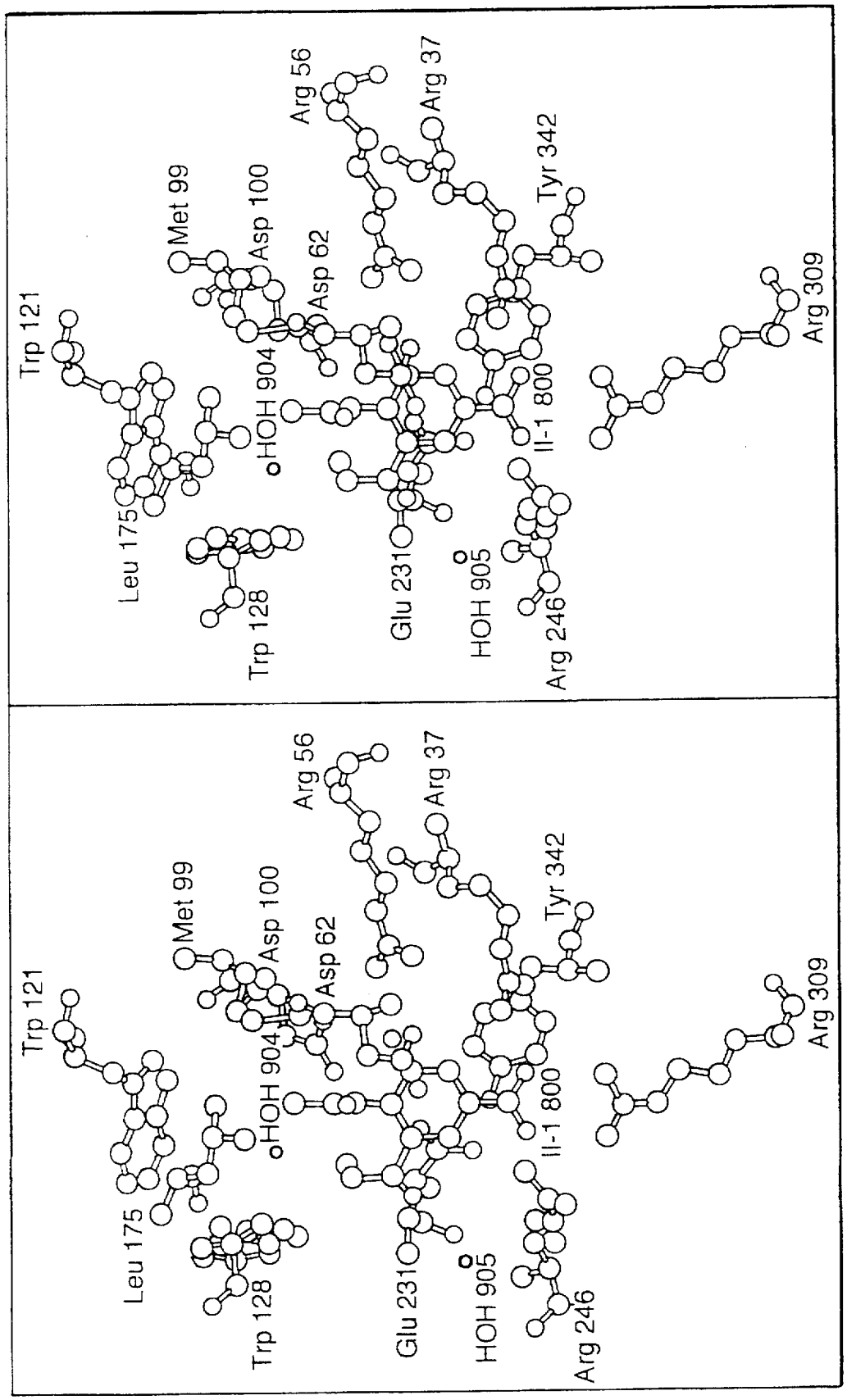
FIG. 4a shows a stereopair view of energy minimized INSA II-1 in the sialidase binding site.

The class 11 compounds (INSA II1, II-2, and II-3) were constructed to take advantage of site A, the very favorable $N3^+$ probe binding site See FIG. 4a The ethylamino sidechains of the class II compounds were modeled into the $N3^+$ pocket where they should make strong electrostatic interactions with the neighboring acidic sidegroups. The $X_1$ groups in the class II series were included to increase the potential interaction energy of the inhibitors by placing hydrogen bonding moieties in pocket B, a favorable OH2 probe binding site. The C5 substitution of the generic structure is shown as $CHX_1CH_2CH_2NH_3^+$ where $X_1$ is OH, $CH_2OH$ or $CH_2OHCH_2OH$. One of skill in the art would recognize that C5 may be substituted by $A_3$ where $A_3$ is alkyl, alkoxy, alkenyl, alkenoxy, alkynyl, or alkynoxy, or alkanol, alkenol, or alkynol of one or more OH moieties on the alkanol, alkenol, or alkynol, where $A_3$ is unbranched or branched, of from 1 to 4 carbons, and $A_3$ is unsubstituted or substituted independently with one or more substitutions of $NH_2$ ($NH_3^+$), COOH, halide, SH, OH, or guanidinium The alcohols listed may have more than one OH moiety.

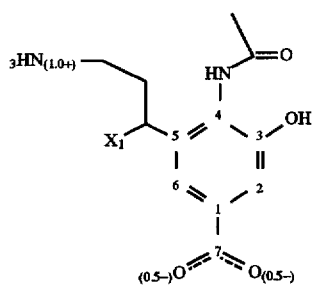

II-1: $X_1 = OH$
II-2: $X_1 = CH_2OH$
II-3: $X_1 = CH_2OHCH_2OH$

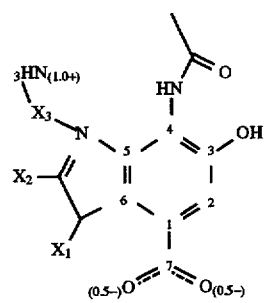

III-1: $X_1 = OH, X_2 = OH, X_3 = CH_2$
III-2: $X_1 = H, X_2 = OH, X_3 = CH_2$
III-3: $X_1 = H, X_2 = CH_2(CH_2OH)_2, X_3 = CH_2$
III-4: $X_1 = H, X_2 = C(CH_2OH)_3, X_3 = CH_2$
III-5: $X_1 = H, X_2 = OH, X_3 = CH_2CH_2$

Figure 4B:
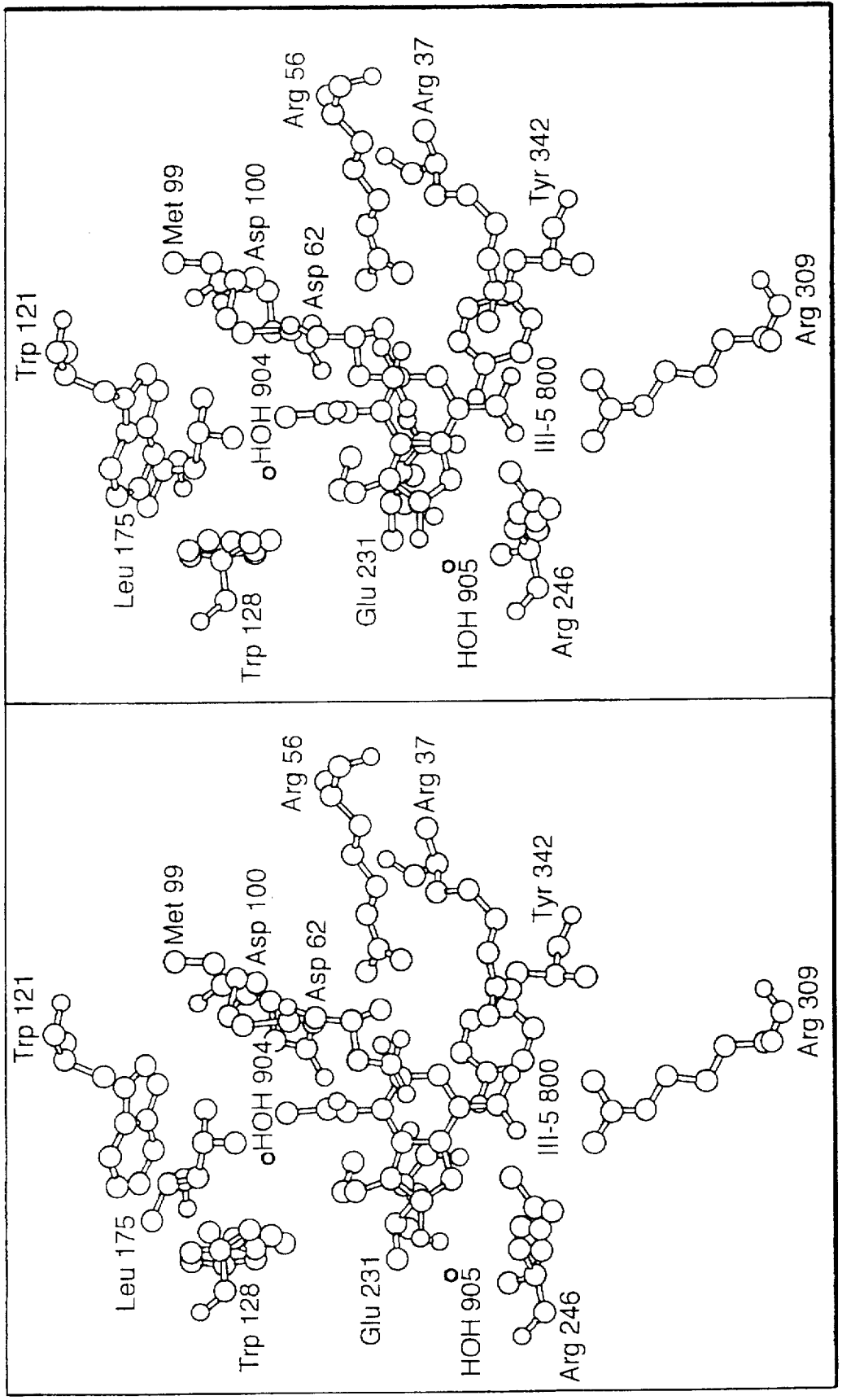
FIG. 4b shows a stereopair view of energy minimized INSA III-5 in the sialidase binding site.

The class III compounds (INSA III-1, III-2, III-3, III-4, and III-5) were also constructed to reach site A, the very favorable $N3^+$ binding site See FIG. 4b. The indole ring system in the class III compounds provides a rigid scaffolding for extending amino sidegroups into site A, as well as, hydrogen bonding groups into site B and possibly site C. The inclusion of a rigid ring system in the class III compounds lowers the entropic cost for inhibitor binding associated reducing conformational degrees of freedom in the bound inhibitor. One of skill in the art would appreciate that the side ring, while shown as a 5-membered ring in the structure below, can be a 4-, 5-, or 6-membered ring, where the ring is saturated, partially unsaturated or fully unsaturated, cyclic or heterocyclic with one to two heteroatoms of O, N, or S substituted for any ring carbon. In the structure shown below, the 5-membered ring is heterocyclic with N substituted for one of the ring carbons The carbon or heteroatom adjacent to C6 can be unsubstituted or substituted independently with one or more substitutions of OH or alkanol, alkenol, or alkynol of one or more OH moieties on the alkanol, alkenol, or alkynol, branched or unbranched, of from 1 to 4 carbons, and the carbon or heteroatom adjacent to C5 is substituted with $X_3NH_3^+$ (as shown in the structure below) or $A_4NH_3^+$, where $A_4$ is alkyl, alkenyl or alkynyl, or alkanol or alkenol of one or more OH moieties on the alkanol or alkenol, of from 1 to 3 carbons, and, for the 5- or 6-membered second ring, the intermediate second ring carbons between $R_4$ and $R_5$ are independently unsubstituted or substituted with one or more substitutions of OH, or alkanol, alkenol or alkynol of one or more OH moieties on the alkanol, alkenol, or alkynol, branched or unbranched, of from 1 to 4 carbons Thus, $X_2$ (a substitution on an intermediate ring carbon) in the structure below can be OH, $CH_2$ $(CH_2OH)_2$, $C(CH_2OH)_3$, etc.

Each INSA compound was constructed using the program QUANTA and modeled into the *S. typhimurium* sialidase active site in a manner similar to HNBA. Water molecules present in the Neu5Ac2en-bacterial sialidase complex were included in the each modeled INSA-bacterial sialidase complex if not sterically excluded by the INSA compound.

J. DELPHI Calculation of Free Energy Change upon Complex Formation for the Modeled INSA-Bacterial Sialidase Complexes For each of the INSA inhibitors, the relative binding affinity of the designed compound was determined without initially undergoing costly and lengthy syntheses. Several methods exist to predict binding affinities, both qualitatively and quantitatively, for modeled inhibitor-protein complexes. The program DELPHI calculates the electrostatic potential of macromolecular systems using a finite difference solution to the non-linear Poisson-Boltzmann equation [Gilson, M. K., & Honig, B., Calculation of the total electrostatic energy of a macromolecular system; solvation energies, binding energies, and conformational analysis. *Proteins: structure, function and genetics,* 4, pp. 7–18 (1988)]. For a given macromolecular inhibitor-protein complex, DELPHI can be used to calculate the total electrostatic energy of the system. For the modeled INSA-bacterial sialidase complexes, the electrostatic contribution to the free energy change upon complex formation, $\Delta G_{el}$, was derived from the total electrostatic energies of three inhibitor complexes: E1, the electrostatic energy of the complex when charges are present only on the protein residues; E2, the electrostatic energy of the complex when charges are present only on the inhibitor residues; and E3, the electrostatic energy of the complex when charges are present on both the protein and inhibitor residues. The free energy change resulting from electrostatic interactions is therefore: $\Delta G_{el}=E_1-(E_2+E_3)$. Because the binding of inhibitors to the bacterial active site is dominated by electrostatic interactions and due the inherent complexity of hydrophobic interactions, the contribution of the hydrophobic effect was not explicitly included in the DELPHI calculation. However, the contribution of the hydrophobic effect to the free energy of complex formation for compounds within a single INSA class, which have a similar functional groups and chemical properties, is roughly on the same order of magnitude. Therefore, exclusion of the hydrophobic contribution to the calculated free energy of complex formation should not change the relative ranking of a series of compounds within any single class.

For each of the modeled INSA-bacterial sialidase complexes, the electrostatic contribution to the change in free energy of complex formation was calculated using a protein/inhibitor dielectric constant of 4, a solvent dielectric constant of 80, an ionic strength of 0.145M, and a focusing protocol of 30–90% fill. Table 1 presents the calculated free energies of complex formation for the proposed INSA-bacterial sialidase complexes, as well as, the calculated free energies of complex formation for the benzoic acid-bacterial sialidase complexes.

and one leucine (Leu 175), where as the vital hydrophobic pocket contains just one tyrosine (which is analogous in position to Trp 128 of *S. typhimurium*), one isoleucine and one arginine sidechain. In addition, several other features can be used to distinguish the *S. typhimurium* bacterial active site from its counterpart in the influenza virus sialidase. For example, there are several significant differences in the active site residues which form the binding pockets for the O4 hydroxyl and glycerol groups of sialic acid. In the bacterial enzyme, an arginine and an aspartic acid residue (Arg 56 and Asp 100 in *S. typhimurium* ), which the vital sialidase does not contain, form strong hydrogen bonds to the O4 atom of the bound sialic acid. The presence of these residues in the bacterial active site also prevent binding of sialic acid analogs modified at the O4 position with large, bulky groups. At the glycerol binding pocket, the bacterial enzyme is lacking a glutamic residue (Glu 275) found in the influenza virus enzyme which provides two hydrogen bonds

TABLE 1

DELPHI electrostatic energies of complex formation for HNBA, GBA, and the INSA series of inhibitors when complexed to bacterial sialidase from *Salmonella typhimurium*.

| Data Set | $E_1$ (kT) | $E_2$ (kT) | $E_3$ (kT) | $\Delta G_{el}$ (kT) | $\Delta G_{el}$ (kcal/mol) | $\Delta(\Delta G)$† (kcal/mol) |
|---|---|---|---|---|---|---|
| GBA | 29341.89 | 99.49 | 29388.96 | −52.42 | −31.09 | −12.87 |
| HNBA | 29438.42 | 107.24 | 29514.95 | −30.71 | −18.21 | 0.00 |
| INSA I-1 | 29370.14 | 96.82 | 29436.5 | −30.46 | −18.06 | 0.15 |
| INSA I-2 | 29393.17 | 104.17 | 29473.08 | −24.26 | −14.39 | 3.82 |
| INSA I-3 | 29379.15 | 106.03 | 29455.7 | −29.48 | −17.48 | 0.73 |
| INSA I-4 | 29362.41 | 111.02 | 29441.14 | −32.29 | −19.15 | −0.94 |
| INSA II-1 | 29373.78 | 125.47 | 29442.27 | −56.98 | −33.79 | −15.58 |
| INSA II-2 | 29400.59 | 117.71 | 29463.3 | −55.00 | −32.62 | −14.40 |
| INSA II-3 | 29322.68 | 129.49 | 29393.28 | −58.89 | −34.92 | −16.71 |
| INSA III-1 | 29337.47 | 119.73 | 29416.36 | −40.84 | −24.22 | −6.01 |
| INSA III-2 | 29349.77 | 121.58 | 29427.53 | −43.82 | −25.99 | −7.77 |
| INSA III-3 | 29303.24 | 138.17 | 29392.56 | −48.85 | −28.97 | −10.76 |
| INSA III-4 | 29266.96 | 123.37 | 29353.29 | −37.04 | −21.96 | −3.75 |
| INSA III-5 | 29391.85 | 126.96 | 29462.2 | −56.61 | −33.57 | −15.36 |

†$\Delta(\Delta G) = \Delta G_{el}(i) - \Delta G_{el}(HNBA)$, where i is any inhibitor.

The partial charges assigned to the INSA compounds in the DELPHI calculation were determined using the semiemperical program MOPAC v6.0 and the coordinates of the final energy minimized inhibitor compound when complexed to *S. typhimurium*. The DELPHI electrostatic energies were calculated using a focusing protocol comprised of three stages of the percent fill: 30%, 60%, and 90%. Using 90% fill in the final stage gave a step size of 1.04 Å. The following parameters were used for all DELPHI calculations: protein dielectric, $e_p$=4, solvent dielectric, $e_s$=80, ionic strength=0.145, linear iterations=1000, and non-linear iterations=3000. Unless otherwise stated, the DELPHI default values were used for all other parameters in the electrostatic free energy calculations.

K. Comparison of Influenza Virus and Bacterial Sialidase Active Sites

As with influenza virus sialidases, the bacterial sialidase active site from *S. typhimurium* also contains an arginine triad (Arg 37, Arg 246, and Arg 309), which binds the carboxylate moiety of sialic acid; a hydrophobic pocket, which accommodates the methyl group of the substrate N-acetylamino moiety; and a tyrosine residue (Tyr 342) located beneath the substrate pocket. Though functionally similar, the residues which compose the hydrophobic pocket differ between the bacterial and viral active sites. The bacterial hydrophobic binding site is composed of two tryptophans (Trp 121, Trp 128), one methionine (Met 99), to the glycerol O8 and O9 atoms of the bound sialic acid. In addition, in the glycerol pocket found in the bacterial sialidase is much larger and broader than the glycerol pocket of influenza virus sialidase due to the alternate orientation of a loop in the bacterial sialidase. In the bacterial enzyme, the loop, comprised of residues 196–205, points away from the active site to create a wide, shallow glycerol binding pocket. The analogous loop in the influenza virus sialidase points toward the active site and effectively limits the size of the pocket to inhibitor sidegroups no longer than glycerol.

L. Targeting of Active Site Regions for Exploitation by Potential Inhibitors

The three new classes of bacterial sialidase-specific inhibitor compounds which are proposed, as well as the generic class depicted as general structure I above, were primarily targeted against site A, the $N3^+$ binding site identified from the GRID analysis, and the active site hydrophobic pocket formed by Trp 121, Trp 128 and Leu 175. These regions of the active site were selected for exploitation on the basis of the relative interaction energies of the GRID probe binding sites, the structural differences between the bacterial and viral sialidases in these regions, and the chemical intuition of the authors.

The GRID map analysis identified the sites with substantial interaction energies in the bacterial sialidase active site. Site A was observed to be a very favorable anionic binding site for the $N3^+$ probe. Site A also includes the binding sites of the crystallographic water molecules HOH 906 and HOH 907. The hydrophilic binding site B was defined by the OH2 probe and includes the binding site for the crystallographic water molecule HOH 905. Site C was another hydrophilic binding site defined by the OH2 map, but this site did not contain any crystallographic water molecule binding sites. Sites D, E, and F, were observed OH2 map and these hydrophilic binding sites form a long hydration channel leading away from the active site. Site D contained the binding site of HOH 904, while sites E and F did not include any crystallographic water molecules. The C3 hydrophobic probe was helpful in identifying the regions of the active site which favored van der Waals interactions. The bacterial sialidase residues which surround the probe binding sites A through F are not conserved in the influenza virus sialidase. Therefore, modification of the lead compounds to include functional groups which chemically mimic the GRID probes and, hence, should strongly interact with the active site residues which form the favorable probe binding sites, results in inhibitors specific for bacterial sialidase and the related trypanosomal trans-sialidase.

M. Analysis of Free Energy of Complex Formation

The calculated free energy change of complex formation for the proposed compounds was used to rank the INSA compounds according to modifications. The calculated values for the free energy of complex formation are overestimated because the contribution of hydrophobic, entropic, and desolvation terms are excluded from the free energy calculations.

The calculated free energy changes of complex formation for the proposed INSA class I, II and III compounds indicate that strong potential inhibitors of bacterial sialidase result when inhibitor constituents establish interactions in the favorable GRID probe binding sites identified in the enzyme active site. The largest contribution to the binding energy is clearly the presence of a positive charge in site & the anionic $N3^+$ binding site formed by the negatively charged Asp 100 and Glu 231 residues. Since a $NH3^+$ probe was used to locate site A, an amino containing sidegroup was the logical choice for incorporation into the lead inhibitor to interact with site A. However, the high inhibition activity of GBA in the inhibition assay suggests that a guanidino group is also suitable for binding in site A. The class II and III compounds, which contain a positively charged amino group, have a substantial increase in calculated binding affinity when compared to the lead compound, HNBA. As a whole, the class II INSA compounds, which have flexible ethylamino sidegroup, display a higher binding affinity for bacterial sialidase than the more rigid indole-based class III compounds. The presence of a flexible linker to connect the amino group to the body of the inhibitor aids in positioning the amino group effectively in the $N3^+$ binding site A. This explains the higher binding affinity of INSA III-5 versus the other class III compounds. In contrast to the other class III compounds, which all have a methylamino group at the indole branch point, the III-5 compound has an ethylamino group which offers more conformational flexibility to reach into the anionic $N3^+$ binding site.

The substitution of a hydrophobic aromatic ring moiety in the class I compounds for the acetyl group present in the lead compounds improves the calculated free energy change of complex formation. The small increase in the predicted binding affinity of the class I compounds versus the lead benzoic acid compounds is due to the fact that the class I furanyl and phenyl constituents make a hydrophobic contribution to inhibitor binding, but hydrophobic effects were not included in the free energy calculations. For similar reasons, compound I-4 has the highest predicted binding affinity of all the class I compounds due to the significant electrostatic contribution which results from placing the phenyl hydroxyl group in the favorable OH2 binding site B. The binding affinity of compound I-4 is increased in comparison to the Neu5Ac2en due to the displacement of HOH 904 in the modeled I-4 bacterial sialidase complex. The release of bound waters has been estimated to contributed at least $-1.8$ kJ/mol to the total energy of the system.

Surprisingly, the predicted binding affinities of the class II and III potential inhibitors were not significantly increased by the placement of hydrogen bonding moieties in binding site B, which was located using a OH2 grid probe. Theoretically, the placement of a hydroxyl group in site B provides a highly favorable interaction which should lower the free energy change associated with complex formation. The minimal contribution to the binding affinity of a hydroxyl group placed in site B versus an amino group placed in site A may reflect the smaller OH2 probe interaction energy for site B versus the quite large $NH_3^+$ probe interaction energy for site A. In addition, the displacement of HOH 905 in several of the class II and III inhibitor-bacterial sialidase complex should also make a favorable contribution to inhibitor binding affinity when compared to Neu5Ac2en.

N. Biological Significance

Bacterial and trypanosomal infections of humans and livestock can result in serious medical complications and economic loss. Though anti-biotics are available for the treatment of bacterial infections, inhibitors of bacterial sialidase may be medically useful where sialidase activity has been correlated with severe bacterial infection pathology.

O. Modeling and Energy Minimization of INSA Compounds

The program QUANTA was used to build the coordinates of the proposed inhibitor compounds and the program X-PLOR was used to energy minimize the coordinates using partial charges derived from the QUANTA template method which uses the CHARM parameter set. The X-PLOR topology and parameter files for the INSA compounds were preferably generated from geometric information retrieved from the Cambridge Structural Database (CSD) or by comparison to analogous structures present in the X-PLOR topology and parameter libraries [Allen, F. H., Davies, J. E., Galloy, J. J., Johnson, O, Kennard, O, Macrae, C. F., Mitchell, E. M., Mitchell, G. F., Smith, J. M. & Watson, D. G., (1991), *J. Chem. Inf. Comp. Sci.* 31:187–204].

The first round of X-PLOR energy minimization consisted of 500 cycles of the conjugate gradient minimization on the free inhibitor coordinates. During this round of minimization, the carboxylate O71-C7C-1-C2 dihedral was restricted to 0.0° and N-acetylamino C3-C4-N4-C8 dihedral was restricted to 90.0°. No other geometric parameters were constrained. The restricted dihedral values are close to the values of the analogous dihedral angles observed in the Neu5Ac2en-*S. typhimunum* complex and provide a standardized geometry for modeling the compounds into the bacterial sialidase active site.

For each energy minimized INSA inhibitor compounds, the C1, O3, and C5 atoms were least squares fitted to the HNBA C1, O3, and C5 atoms in the HNBA-bacterial sialidase complex. For each INSA-bacterial sialidase complex, water molecules present in the Neu5Ac2en-*S. typhimurium* bacterial sialidase complex which did not sterically conflict with the modeled INSA compound were included in the inhibitor complex.

To relieve potentially poor contacts resulting from the initial superposition of the INSA compounds in the *S. typhimurium* active site, the INSA compound-bacterial sialidase complexes were energy minimized for 100 cycles using the Powell method using the program X-PLOR. A harmonic restraint of 500 kcal/mol was placed on all atoms more than 10Å distant from the INSA compound, while no harmonic constraints were applied to atoms within 10Å of the INSA compound. No geometric restrictions were applied to the INSA compounds during the energy refinement of the modeled INSA *S. typhimurium* complexes. Also, the partial charges assigned to the aspanic acid, glutamic acid, lysine, and arginine protein sidechains, as well as, the INSA amino group when present, were set to zero during the energy minimization of the modeled INSA *S. typhimurium* complexes.

P. Syntheses of Benzenoid Inhibitors

The compounds of the instant invention, including pharmaceutically acceptable salts, analogs and derivatives, may be prepared using any of several methods known in the art for the synthesis of substituted benzenoid compounds containing analogous structures.

The following synthesis are put forth so as to provide those of ordinary skill in the an with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, pans are pans by weight, temperature is in ° C. and pressure is at or near atmospheric.

To illustrate, potential synthetic approaches for selected examples from General Structure I are summarized in the following reaction schemes and are representative of the types of procedures to be employed. The following detailed examples for methods of preparation are for illustration only, and are not intended to represent a limitation of the invention.

1) Synthesis of Benzenoid Inhibitors

Compounds with Structure A and their pharmaceutically acceptable salts, analogs and derivatives may be prepared using any of the several methods known in the art for the synthesis of substituted benzenoid compounds containing analogous structures.

Structure A:

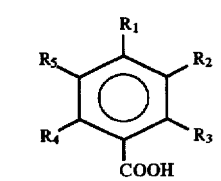

The structures or the potential benzenoid inhibitors 1–4 are set forth in Table 2 The potential synthetic strategies are summarized by FIGS. 1 and 2 and the accompanying text.

TABLE 2

| Compound | $R_1$ | $R_2$ | $R_3$ | $R_4$ | $R_5$ |
|---|---|---|---|---|---|
| 1 | (4-hydroxyphenyl)amino | OH | H | H | $NO_2$ |
| 2 | (2-pyrimidinyl)amino | OH | H | H | $NO_2$ |
| 3 | (4-pyridyl)amino | OH | H | H | $NO_2$ |
| 4 | amino-acetyl | OH | H | H | $CH_2CH_2NH_2$ | a) Synthesis of Benzenoid Inhibitors 1–3

Vanillic acid can be converted to compound 5 via nitration [I. Pearl, *J. Amer. Chem. Soc.* 1946, 68, 1100] followed by esterification (Table 3). Tosylation of 5 to 6 is known to one of skill in the art. Aromatic nucleophilic substitution reaction between 6 and p-anisidine, or 2-aminopyrimidine, or 4-aminopyridine, respectively, will afford the penultimate derivatives 7–9 [M. d'Alarcao, et al; *J. Org. Chem.* 1985, 50, 2456–2461]. Deprotection to the target compounds 1–3 will occur via treatment with lithium iodide in s-collidine [Harrison, *Chem. Commun.* 1969, 616; Elsinger, et al.; *Helv. Chim. Acta*, 1960, 43, 113].

b) Synthesis of Benzenoid Inhibitor 4

Previously described compound 10 will be iodinated, saponified, and protected to provide 11 (Table 4). Conversion of 11 to 12 can be achieved by the Heck reaction between acrylic acid and 11 [Y. Hatanaka, et al; *J. Amer. Chem. Soc.* 1991, 113, 7075–7076], followed by reduction with Raney nickel and hydrogen. The Weinstock modification of the Curtius reaction followed by trapping of the intermediate isocyanate with benzyl alcohol will be used to convert 12 to compound 13 [T. Capson, et al; *Tetrahedron Lett.* 1984, 25, 3515–3518]. Palladium catalyzed hydrogenation will afford target 4 from 13.

TABLE 3

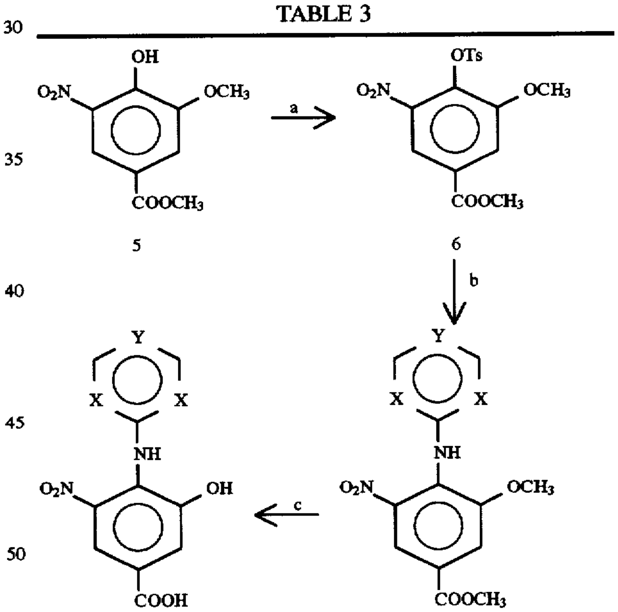

5

6

1: X = CH, Y = C—OH
2: X = N, Y = C—H
3: X = CH, Y = N

7: X = CH, Y = C—OCH₃
8: X = N, Y = C—H
9: X = CH, Y = N

Ts = p-toluenesulfonyl
Bn = benzyl
a. Tosylation
b. Nucleophilic aromatic substitution
c. Lithium iodide, s-collidine

TABLE 4

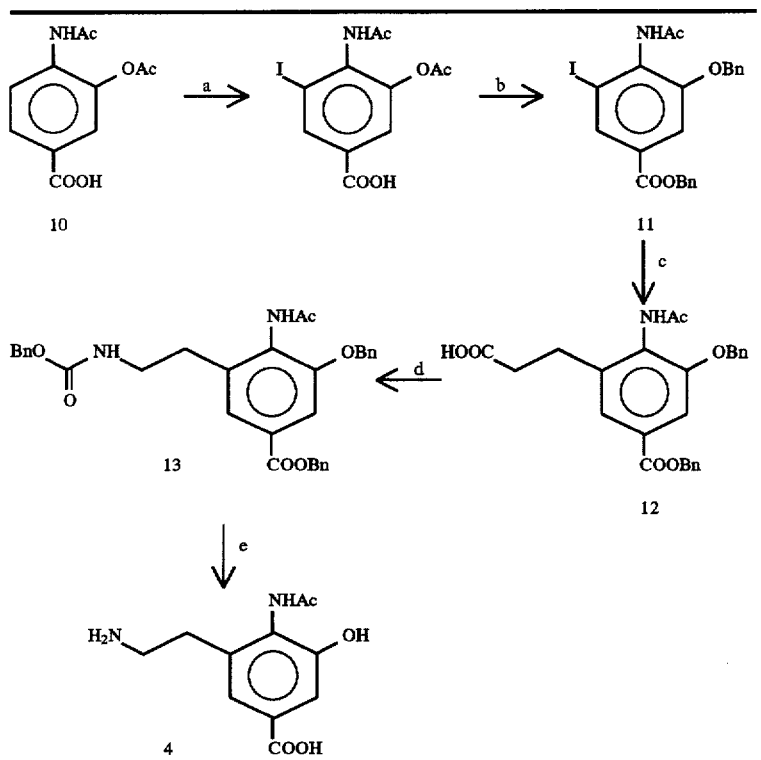

a: (i) Iodination, (ii) saponification, (iii) protection b: (i) Heck reaction coupling, (ii) reduction c: Weinstock-Curtius reaction d: Palladium-catalyzed hydrogenation 2) Synthesis of Indole Inhibitors Compounds with Structure B and their pharmaceutically acceptable salts, analogs and derivatives may be prepared using any of the several methods known in the art for the synthesis of substituted indole compounds containing analogous structures.

Structure B:

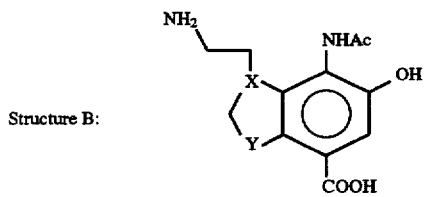

The structures of the potential indole inhibitors 14–15 are set forth in Table 5. The potential synthetic strategies are summarized by Tables 6, 7, and 8 and the accompanying text.

TABLE 5

| Compound | X | Y |
|---|---|---|
| 14 | N | —CH |
| 15 | —C | NH | a) Synthesis of Indole Inhibitor 14

The synthesis of 14 can be patterned after the methods of Nichols et al. for the synthesis of alkyltryptamine derivatives [D. Lloyd, D. Nichols; *J. Org. Chem.* 1986, 51, 4294–4295], (Table 6). 2-Methyl-5-nitrobenzoic acid will be converted to 16 by standard chemical methods. In a similar matter, 16 will be converted to 17 by sequential nitration, protection, reduction and acetylation. Nitration of 17 will provide the key intermediate 18. The method of Nichols, et al. will provide indole 19 from 18. Selective alkylation of the indole nitrogen with protected 2-chloroethanol will afford 20. Conversion of 20 to 21 is known to one of skill in the art. Catalytic hydrogenation of 21 will provide target 14.

b) Synthesis of Indole Inhibitor 15

The synthesis of 15 can be approached via two separate routes (Tables 7 and 8). The first approach entails the Heck reaction coupling of 11 with acrylonitrile to afford 22. Reduction of 22 followed by protection of the primary amine will provide 23. The conversion of 23 to the substituted indole 24 will occur via the method of Nichols, et al.

Catalytic hydrogenation will afford target 15. In the event that the approach outlined previously is unsuccessful or inefficient, the more classical approach outlined in Table 8 can be used. 3-Methyl-4-nitrobenzoic acid can be converted by sequential reduction, acetylation, nitration to 25. Reduction, conversion to the phenol, followed by protection will afford 26 from 25. Nitration of 26 will provide 27. The conversion of 27 to indole 28 will be achieved by methods previously outlined herein. The conversion of 27 to target 15 is anticipated via well established methods.

TABLE 6

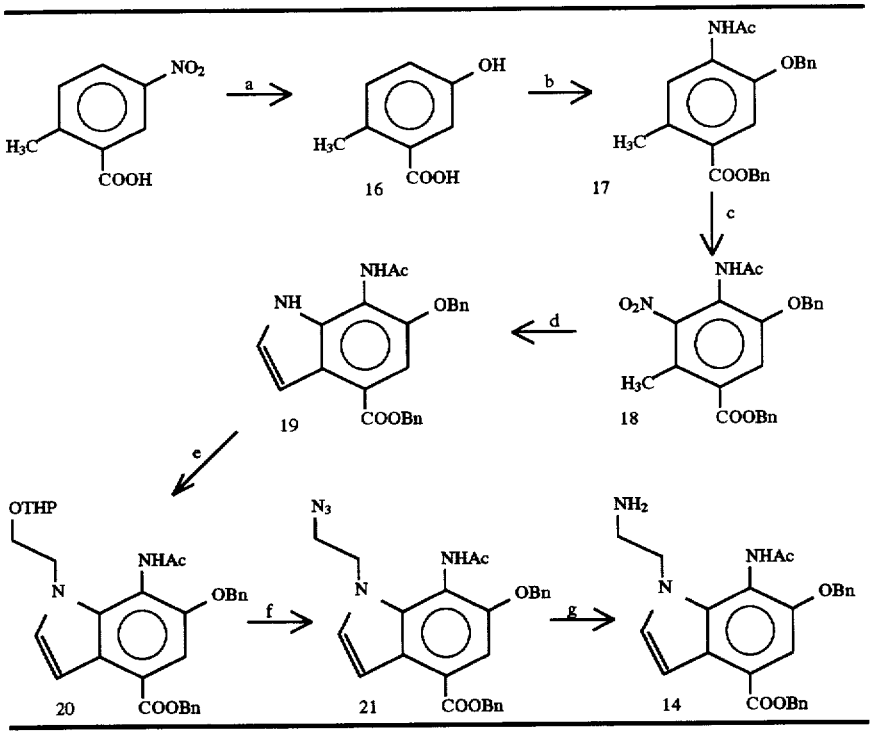

THP = tetrahydropyranyl a: (1) Reduction, (ii) conversion to phenol b: (i) Nitration, (ii) protection, (iii) reduction, (iv) acetylation c: Nitration d: Conversion to indole e: Alkylation f: Conversion to azide g: Catalytic hydrogenation

TABLE 7

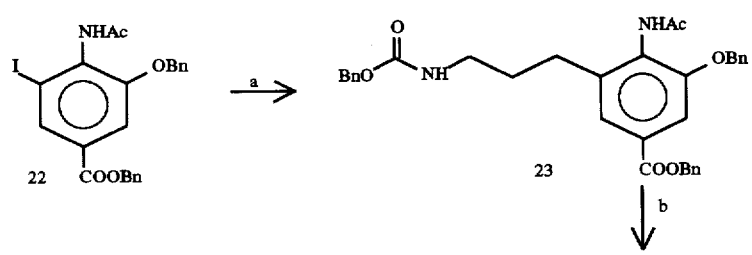

TABLE 7-continued

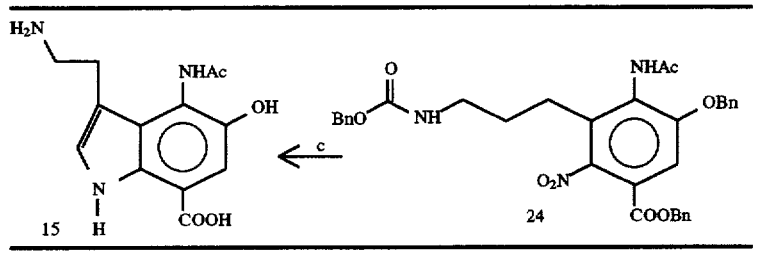

a: (i) Heck reaction coupling, (ii) reduction, (iii) protection b: Conversion to indole c: Catalytic hydrogenation

TABLE 8

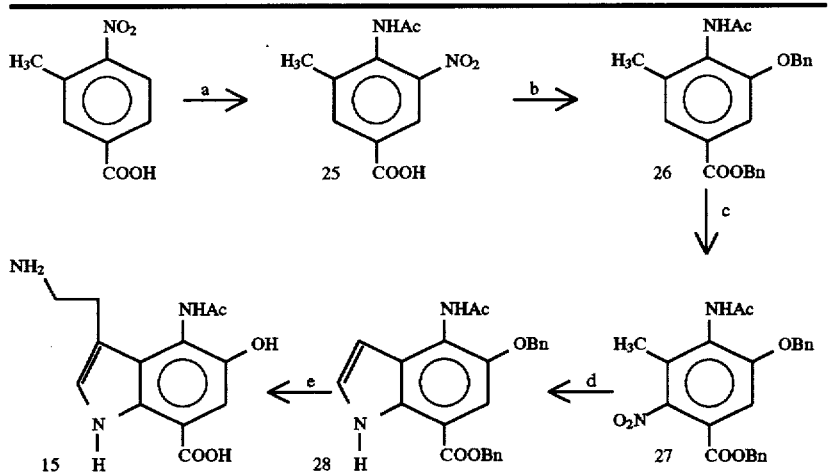

a: (i) Reduction, (ii) acetylation, (iii) nitration b: (i) Reduction, (ii) conversion to phenol, (iii) protection c: Nitration d: Conversion to indole e: Manipulation to target 15

Q. Modes of Administration

As used herein, the effective amount of a compound of the invention required for use in the methods described herein will vary not only with the particular compound selected but also with the mode of administration, the nature of the condition in the subject, and the age and health of the subject. The exact dosage will ultimately be determined by a physician or other person skilled in the art. However, a suitable systemic dose will generally range from about 0.01 to about 200 mg/kg of bodyweight per day. More preferably, an effective mount (suitable dose) will range from 0.1 to 50 mg/kg/day. Treatment may occur before bacterial infection (i.e. prophylaxis), at the start of infection, or after the onset of established symptoms or infection. Treatment with the effective amount may be given 1 to 4 times daily and the typical duration will range from 3 to 10 days, or until bacteria or trypanosoma are no longer present and/or symptoms have disappeared. Furthermore, a suitable topical dose will generally range from approximately 1 nM to 1 mM. Treatment may occur before bacterial infection (i.e. prophylaxis), at the start of infection, or after the onset of established symptoms or infection. Treatment with the effective amount may be given 1 to 4 times daily and the typical duration will range from 3 to 10 days, or until bacteria or trypanosoma are no longer present and/or symptoms have disappeared. Those skilled in the art will recognize that deviations from the above described treatment methods and effective amounts are possible and are to be included in the subject matter taught herein.

Furthermore, it is possible that, during therapy, the compounds may be administered alone as pure chemical or as a pure pharmaceutically acceptable salt, analog or derivative. However, it is preferable to provide the active chemical, or its pharmaceutically acceptable salt, analog or derivative, as a pharmaceutical formulation, either as a dry powder (tablet or capsule form or with a suitable carrier), or as a solution or suspension (in water or in physiologically acceptable solvents or cosolvents such as ethanol, propylene glycol, or PEG 400). The appropriate pharmaceutical formulation may be administered by topical, oral, intranasal, intravenous, intramuscular or other appropriate modes. A preferred mode of administration for treating a bacterial infection is to topically apply the inhibitor to the infected region of the subject. The desired dosage (effective amount) may be administered in one or in divided doses at appropriate intervals each day. The compounds and compositions of the invention may also be administered in combination with other therapeutic agents. Those skilled in the art will appreciate that dosages and modes of administration are readily determinable without undue experimentation.

The compounds of the invention may be conveniently formulated into pharmaceutical compositions composed of one or more of the compounds in association with a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that may be used in conjunction with the preparation of formulations of the inventive compounds and which is incorporated by reference herein.

In preferred embodiments, the compounds of the present invention can be delivered in the following manners:

1. Oral/Pill
2. Nasal Aerosol
3. Ear/Eye Drops
4. Topical Cream
5. Intravenous Solution
6. Suppository
7. Dental Mouthwash These methods of drug delivery may be practiced with standard pharmacological formulations.

R. Conditions Treated or Prevented

The compounds of the invention provide a broad range of anti-bacterial and anti-trypanosomal activity. The compounds should inhibit bacterial sialidase and trypanosomal trans-sialidase. The medical benefits which result from inhibition of sialidase/trans-sialidase activity may vary as they are dependent on the specific organism. Examples where sialidase/trans-sialidase activity has been documented to play a role in the pathology are listed below. One skilled in the art would recognize that treatment with the compounds to inhibit the sialidase/trans-sialidase activity in these cases would prove beneficial.

The present compounds may be used in methods of preventing of bacterial or trypanosome adherence. In the following examples, the organism requires the sialidase/ trans-sialidase activity to attach to the cells of the host prior to invasion. The treatment with compounds would therefore be expected to prevent or limit infection of the host by the microorganism, but not directly kill the microorganism. Treatments, or prophylaxis, of the following infections would be expected to be effective:

a) dental caries/bacterial-mediated gum disease [Childs, W. d. & Gibbons, R. J. 1990). Selective modulation of bacterial attachment to oral epithelial cells by enzyme activities associated with poor oral hygiene. *J Period. Res.*, 25, pp. 172–8.; Liljemark, W. F., Bloomquist, C. G., Fenner, L. J., Antonelli, P. J. & Coulter, M. C. (1989). Effect of neuraminidase on the adherence to salivary pellicle of Streptococcus sanguis and Streptococcus mitis. *Caries Res.*, 23, pp. 141–5; Rogers, R., Newbrun, E. & Tatevossian, A. (1979). Neuraminidase activity in human dental plaque fluid. *Archives of Oral Biology* 24(9), 703–5]. Mode of delivery: dental mouthwash;

b) arteritis [Nakato, H., Shinomiya, K. & Mikawa, H. (1986). Possible role of neuraminidase in the pathogenesis of arteritis and thrombocytopenia induced in rats by Erysipelothrix rhusiopathiae. *Pathol Res Pract.*, 181, pp. 311–9]. Modes of delivery: oral pill, intravenous solution;

c) Pseudomonas aeruginosa infection in cystic fibrosis (CF) [Cacalano, G., Kays, M., Saiman, L. & Prince, A. (1992). Production of the Pseudomonas aeruginosa neuraminidase is increased under hyperosmolar conditions and is regulated by genes involved in alginate expression. *Journal of Clinical Investigation* 89(6), 1866–74]. Modes of delivery: oral pill, intravenous solution, nasal aerosol;

d) *Actinomyces viscosus* and *A. naeslundii* infection [Costello, AH, Cisar, J, Kolenbrander, PE & Gabriel, O (1979). Neuraminidase-dependent hemagglutination of human erythrocytes by human strains of Actinomyces viscosus and Actinomyces naeslundii. *Infection & Immunity* 26(2), 563–72]. Modes of delivery: oral pill, intravenous solution, topical cream;

e) Bacteroides fragilis infection [Guzman, C. A., Plate, M. & Pruzzo, C. (1990). Role of neuraminidase-dependent adherence in Bacteroides fragilis attachment to human epithelial cells. *Ferns Microbio Lett.*, 59, pp. 187–92; Namavar, F., Van der Bijl, M. W., Appelmelk, B. J., De Graaff, J. & MacLaren, D. M. (1994). The role of neuraminidase in haemagglutination and adherence to colon WiDr cells by *Bacteroides fragilis*. *J Med Microbiol.*, 40, pp. 393–6]. Modes of delivery: oral pill, intravenous solution, topical cream; and f) Chagas' Disease, *Trypanosoma cruzi* infection [de Titto & Araujo, 1987; Ming et al., 1993; Prioli et al., 1991]. Modes of delivery: oral pill, intravenous solution.

Furthermore, the inhibitors can be used in the prevention of bacterial vaginosis. In this example, sialidase is highly correlated with the progress of the disease. The most probable role of sialidase is for successful attachment and colonization of the upper and lower genital tract. Therefore, treatment with the compounds would be expected primarily to prevent or slow the progress of bacterial infection to allow the host's immune system time to recover. A second, but important result of treatment with the compounds of the invention would be to reduce the symptoms associated with bacterial vaginosis (rash, itching, discharge, etc.) [Briselden, A. M., Moncla, B. J., Stevens, C. E. & Hillier, S. L. (1992). Sialidases (neuraminidases)in bacterial vaginosis and bacterial vaginosis-associated microflora. *J Clin Microbiol.*, 30, pp. 663–6; McGregor, J. A., et al. (1994). Bacterial vaginosis is associated with prematurity and vaginal fluid mucinase and sialidase: results of a controlled trial of topical clindamycin cream. *Am J Obstet Gynecol.*, 170, pp. 1048–59]. Modes of delivery: topical cream, suppository, oral pill.

Also, the present inhibitors can be used for the prevention of inner ear effusion. Sialidase activity has been correlated with the development of acute and chronic otitis in inner ear effusions. Treatment with the compounds would therefore prevent the damage to the inner ear mucosa and prevent otitis from developing. It would not directly kill the organism causing the infection [LaMarco, K. L., Diven, W. F. & Glew, R. H. (1986). Experimental alteration of chinchilla middle ear mucosae by bacterial neuraminidase. *Ann Otol*

*Rhinol Laryngol.*, 95, pp. 304–8; LaMarco, K. L., Diven, W. F., Glew, R. H., Doyle, W. J. & Cantekin, E. I. (1984). Neuraminidase activity in middle ear effusions. *Annals of Otology, Rhinology & Laryngology* 93(1 Pt 1), 76–84]. Modes of delivery: Ear drops, oral pill Prevention of arthritis symptoms. Sialidase activity has been correlated with the disease severity in arthritic rats. The effect of treatment with the compounds may reduce the symptoms associated with arthritis, such as lymphocyte activation and swelling [Marchand, N. W., Kishore, G. S. & Carubelli, R. (1978). Neuraminidase activity in the blood and liver of arthritic rats. *Experimental & Molecular Pathology* 19(3), 273–80]. Modes of delivery: oral pill, intravenous solution, topical cream.

Prevention of hemolytic uremic syndrome (HUS) in patients with pneumonia and hemolytic anemia. Sialidases have been implicated as the agent which exposes the Thomsen cryptantigen. Treatment with the compounds would reduce the prevalence of patients developing hemolytic uremic syndrome, but not cure the underlying causes [Seger, R., Joller, P., Baerlocher, K., Kenny, A., Dulake, C., Leumann, E., Spierig, M. & Hitzig, W. H. (1980). Hemolytic-uremic syndrome associated with neuraminidase-producing microorganisms: treatment by exchange transfusion. *Helvetica Paediatrica Acta* 35(4), 359–67]. Modes of delivery: oral pill, intravenous solution Prevention of group B streptococci infection in neonates. The high levels of sialidase activity have been associated with severe group B streptococci infection in infants, where streptococci infection can lead to diarrhea, weight loss, or more severe complications. Treatment with the compounds would prevent bacterial spread and reduce the symptoms associated with the disease in infants [Milligan, T. W., Baker, C. J., Straus, D. C. & Mattingly, S. J. (1978). Association of elevated levels of extracellular neuraminidase with clinical isolates of type III group *B streptococci*. *Infection & Immunity* 21(3), 738–46]. Modes of delivery: intravenous solution, suppository Prevention of acute poststreptococcal glomerulonephritis. The sialidase activity of virulent streptococcal infections has been shown to play a role in the development of acute poststreptococcal glomerulonephritis. It would therefore follow that compound treatment would decrease the likelihood of developing acute poststreptococcal glomerulonephritis [Mosquera, J. & Rodriguez-Iturbe, B. (1984). Extracellular neuraminidase production of streptococci associated with acute nephritis. *Clin Nephrol.*, 21, pp. 21–8; Mosquera, J. A., Katiyar, V. N., Coello, J. & Rodriguez-Iturbe, B. (1985). Neuraminidase production by streptococci from patients with glomerulonephritis *Journal of Infectious Diseases* 151 (2), 259–63; Potter, E. V., Shaughnessy, M. A., Poon-King, T. & Earle, D. P. (1982). Streptococcal neuraminidase and acute glomerulonephritis. *Infection & Immunity* 38(3), 1196–1202]. Modes of delivery: intravenous solution, oral pill Prevention of acne and seborrheic eczema. Sialidase activity has been highly associated with Propionibacterium acnes-strains isolated from patients with acne vulgaris, seborrheic eczema and healthy subjects. Treatment with the compounds of the invention should therefore prevent or decrease infection by the Propioniobacterium aches bacterium. It should also alleviate some of the symptoms associated with ache [Hoffler, U., Gloor, M. & von Nicolai, H. (1981). Neuraminidase production by Propionibacterium acnes-strains isolated from patients with acne vulgaris, seborrheic eczema and healthy subjects. *Zentralblatt Fur Bakteriologie, Mikrobiologie Und Hygiene* 250(1–2), 122–6; von Nicolai, H., Hoffler, U. & Zilliken, F (1980) Isolation, purification, and properties of neuraminidase from Propionibacterium acnes *Zentralblatt Fur Bakteriologie* 247 (1), 84–94]. Modes of delivery: topical cream, oral pill Prevention of arteritis. *Erysipelothrix rhusiopathiae* induced arteritis was highly correlated to production of sialidase by the bacteria. Treatment would therefore inhibit bacterial sialidase, attachment, and infection of aortic tissue. [Nakato et al., 1986; Nakato, H., Shinomiya, K. & Mikawa, H. (1987). Adhesion of *Erysipelothrix rhusiopathiae* to cultured rat aortic endothelial cells. Role of bacterial neuraminidase in the induction of arteritis. *Pathology, Research & Practice* 182(2), 255–60]. Modes of delivery: oral pill, intravenous solution.

This invention thus describes classes of bacterial sialidase inhibitors, their pharmaceutically acceptable salts and derivatives, and mixtures thereof having general structure I. These inhibitors may be used in a variety of methods as described herein.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A sialidase inhibitor of formula I:

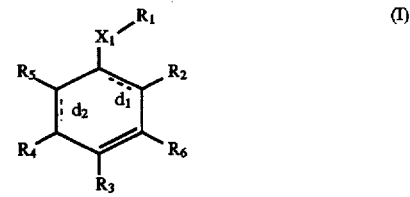

wherein the dashed lines $d_1$ and $d_2$ are unsaturations;

$X_1$ is NH;

$R_1$ is a 5-, 6-, or 7-membered first ring, saturated or unsaturated, unsubstituted or substituted independently with one or more substitutions of (a) OH or (b) a branched or unbranched, alkyl, alkenyl or alkynyl of from 1 to 6 carbons, unsubstituted or substituted independently with one or more substitutions of OH, SH, $NH_2$ or halide, where the 5-, 6-, or 7-membered first ring is carboxyclic or heterocyclic with one to two heteroatoms of O, N, or S;

$R_2$ is OH or $NH_2$;

$R_6$ is H, OH, SH, $NH_2$, halide, or $A_2$ where $A_2$ is alkyl, alkoxy, alkenyl, alkenoxy, alkynyl, or alkynoxy, or alkanol, alkenol, or alkynol of one or more OH moieties on the alkanol, alkenol, or alkynol, where $A_2$ is unbranched or branched, of from 1 to 4 carbons, and $A_2$ is unsubstituted or substituted independently with one or more substitutions of $NH_2$, COOH, halide, SH, OH, or guanidinium;

$R_3$ is COO$^-$, POO$^-$, BOO$^-$ or SOO$^-$ where the corresponding cation is H or a salt; and

39

$R_4$ is H and $R_5$ is $NO_2$,
an analog, pharmaceutically acceptable salt, or derivative of the inhibitor of the formula I, with the proviso that the compound wherein $R_1$ is phenyl, $R_2$ is $NH_2$, $R_6$ is H, and $R_3$ is COO wherein the corresponding cation is H or a salt thereof are excluded.

2. The sialidase inhibitor of claim 1, wherein $R_1$ is a furanyl- or phenyl-, unsubstituted or substituted with OH, $CH_3$ or glycerol; $R_6$ is H; and $R_3$ is $COO^-$ where the corresponding cation is H or a salt.

3. The sialidase inhibitor of claim 1, wherein $R_1$ is unsubstituted furanyl-; $R_2$ is OH; $R_6$ is H; and $R_3$ is $COO^-$ where the corresponding cation is H or a salt.

4. The sialidase inhibitor of claim 1, wherein $R_1$ is mono- or dimethyl-substituted furanyl-; $R_2$ is OH; $R_6$ is H; and $R_3$ is $COO^-$ where the corresponding cation is H or a salt.

5. The sialidase inhibitor of claim 1, wherein $R_1$ is p-hydroxyphenyl-; $R_2$ is OH; $R_6$ is H; and $R_3$ is $COO^-$ where the corresponding cation is H or a salt.

6. A pharmaceutical composition for inhibiting bacterial or trypansomal sialidase, comprising an inhibiting effective amount of a compound of claim 1 and a pharmaceutically acceptable carrier.

7. A method of inhibiting bacterial or trypanosomal sialidase, comprising administering to a subject in need thererof an inhibiting effective amount of a compound of formula I:

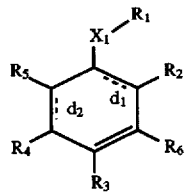
(I)

wherein the dashed lines $d_1$ and $d_2$ are independently unsaturations or saturations and the core ring is carbocyclic or heterocyclic with one to two heteroatoms of O, N, or S;

$X_1$ is CO, $SO_2$, NH, $CH_2$, S, or O;

$R_1$ is $NH_2$, SH, $OCH_3$, halide,
 $COA_1$, where $A_1$ is branched or unbranched, alkyl, alkenyl or alkynyl of from 1 to 5 carbons, and $A_1$ is unsubstituted or substituted independently with one or more substitutions of OH, SH, $NH_2$ or halide,
 a branched or unbranched, alkyl, alkenyl or alkynyl of from 1 to 6 carbons, unsubstituted or substituted independently with one or more substitutions of OH, SH, $NH_2$ or halide, or
 a 5-, 6-, or 7-membered first ring, saturated or unsaturated, unsubstituted or substituted independently with one or more substitutions of
  (a) OH or
  (b) a branched or unbranched, alkyl, alkenyl or alkynyl of from 1 to 6 carbons, unsubstituted or substituted independently with one or more substitutions of OH, SH, $NH_2$ or halide,
where the 5-, 6-, or 7-membered first ring is carbocyclic or heterocyclic with one to two heteroatom of O, N, or S;

$R_2$ and $R_6$ are independently H, OH, SH, $NH_2$, halide, or $A_2$ where $A_2$ is alkyl, alkoxy, alkenyl, alkenoxy, alkynyl, or alkynoxy, or alkanol, alkenol, or alkynol of one or more OH moieties on the alkanol, alkenol, or alkynol, where $A_2$ is unbranched or branched, of from 1 to 4 carbons, and $A_2$ is unsubstituted or substituted independently with one or more substitutions of $NH_2$, COOH, halide, SH, OH, or guanidinium;

40

$R_3$ is $COO^-$, $POO^-$, $BOO^-$ or $SOO^-$ where the corresponding cation is H or a salt; and wherein
A) $R_4$ is H and $R_5$ is $NO_2$;
B) $R_4$ is H, OH, SH, halide, COOH, guanidinium, or alkanol of one or more OH moieties, branched or unbranched; of from 1 to 4 carbons, and $R_5$ is $A_3$ where $A_3$ is alkyl, alkoxy, alkenyl, alkenoxy, alkynyl, or alkynoxy, or alkanol, alkenol, or alkynol of one or more OH moieties on the alkanol, alkenol, or alkynol, where $A_3$ is unbranched or branched, of from 1 to 4 carbons; and $A_3$ is unsubstituted or substituted independently with one or more substitutions of $NH_2$, COOH, halide, SH, OH, or guanidinium; or
C) $R_4$ is C, CH, or $CH_2$ and $R_5$ is CH, or $CH_2$, and $R_4$ forms a 4-, 5-, or 6-membered second ring with $R_5$, where the second ring is saturated, partially unsaturated or fully unsaturated carbocyclic or heterocyclic with one to two heteroatoms of O, N, or S substituted for any second ring carbon, and $R_4$ is unsubstituted or is substituted independently with one or more substitutions of OH or alkanol, alkenol, or alkynol of one or more OH moieties on the alkanol, alkenol, or alkynol, branched or unbranched; of from 1 to 4 carbons, and $R_5$ is substituted with $A_4NH_3^+$, where $A_4$ is alkyl, alkenyl or alkynyl, or alkanol or alkenol of one or more OH moieties on the alkanol or alkenol, or from 1 to 3 carbons, and, for the 5- or 6-membered second ring; the intermediate second ring carbons between $R_4$ and $R_5$ are independently unsubstituted or substituted with one or more substitutions of OH, or alkanol, alkenol or alkynol of one or more OH moieties on the alkanol, alkenol, or alkynol, branched or unbranched, of from 1 to 4 carbons; or an analog, pharmaceutically acceptable salt, or derivative of the inhibitor of the formula I.

8. The method of claim 7, wherein $R_4$ is H and $R_5$ is $NO_2$.

9. A method of making a composition for inhibiting bacterial or trypanosomal sialidase, comprising admixing an inhibiting effective amount of a compound of formula I:

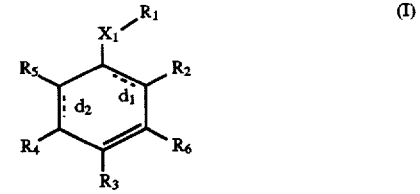
(I)

wherein the dashed lines $d_1$ and $d_2$ are independently unsaturations or saturations and the core ring is carbocyclic or heterocyclic with one to two heteroatoms of O, N, or S;

$X_1$ CO, $SO_2$, NH, $CH_2$, S, or O;

$R_1$ is $NH_2$, SH, $OCH_3$, halide,
 $COA_1$, where $A_1$ is branched or unbranched, alkyl, alkenyl or alkynyl of from 1 to 5 carbons, and $A_1$ is unsubstituted or substituted independently with one or more substitutions of OH, SH, $NH_2$ or halide,
 a branched or unbranched, alkyl, alkenyl or alkynyl of from 1 to 6 carbons, unsubstituted or substituted independently with one or more substitutions of OH, SH, $NH_2$ or halide, or
 a 5-, 6-, or 7-membered first ring, saturated or unsaturated, unsubstituted or substituted independently with one or more substitutions of
  (a) OH or
  (b) a branched or unbranched, alkyl, alkenyl or alkynyl of from 1 to 6 carbons, unsubstituted or substituted independently with one or more substitutions of OH, SH, NH$_2$ or halide, where the 5-, 6-, or 7-membered first ring is carbocyclic or heterocyclic with one to two heteroatoms of O, N, or S;

R$_2$ and R$_6$ are independently H, OH, SH, NH$_2$, halide, or A$_2$ where A$_2$ is alkyl, alkoxy, alkenyl, alkenoxy, alkynyl, or alkynoxy, or alkanol, alkenol, or alkynol of one or more OH moieties on the alkanol, alkenol, or alkynol, where A$_2$ is unbranched or branched, of from 1 to 4 carbons, and A$_2$ is unsubstituted or substituted independently with one or more substitutions of NH$_2$, COOH, halide, SH, OH, or guanidinium;

R$_3$ is COO$^-$, POO$^{31}$, BOO$^-$ or SOO$^-$ where the corresponding cation is H or a salt; and wherein A) R$_4$ H and R$_5$ is NO$_2$;

B) R$_4$ is H, OH; SH, halide, COOH, guanidinium, or alkanol of one or more OH moieties, branched or unbranched, of from 1 to 4 carbons, and R$_5$ is A$_3$ where A$_3$ is alkyl, alkoxy, alkenyl, alkenoxy, alkynyl, or alkynoxy, or alkanol, alkenol, or alkynol of one or more OH moieties on the alkanol, alkenol, or alkynol, where A$_3$ is unbranched or branched, of from 1 to 4 carbons, and A$_3$ is unsubstituted or substituted independently with one or more substitutions of NH$_2$, COOH, halide, SH, OH, or guanidinium; or C) R$_4$ is C, CH, or CH$_2$ and R$_5$ is CH, or CH$_2$, and R$_4$ forms a 4-, 5-, or 6-membered second ring with R$_5$, where the second ring is saturated, partially unsaturated or fully unsaturated, carbocyclic or heterocyclic with one to two heteroatoms of O, N, or S substituted for any second ring carbon; and R$_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and R$_5$ is substituted with A$_4$NH$_3^+$, where A$_4$ is alkyl, alkenyl or alkynyl or alkanol or alkenol of one or more OH moieties on the alkanol or alkenol, of from 1 to 3 carbons, and, for the 5- or 6-membered second ring, the intermediate second ring carbons between R$_4$ and R$_5$ are independently unsubstituted or substituted with one or more substitutions of OH, or alkanol, alkenol or alkynol of one or more OH moieties on the alkanol, alkenol, or alkynol, branched or unbranched, of from 1 to 4 carbons; or an analog, pharmaceutically acceptable salt, or derivative of the inhibitor of the formula I, with a pharmaceutically effective carrier.

10. The method of claim 9, wherein R$_4$ is H and R$_5$ is NO$_2$.

11. A method of preventing bacterial or trypanosomal infection, comprising administering to a subject in need thereof a preventative effective amount of a compound of formula I:

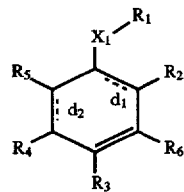

(I)

wherein the dashed lines d$_1$ and d$_2$ are independently unsaturations or saturations and the core ring carbocyclic or heterocyclic with one to two heteroatoms of O, N, or S;

X$_1$ is CO, SO$_2$, NH, CH$_2$, S, or O;

R$_1$ is NH$_2$, SH, OCH$_3$, halide,

COA$_1$, where A$_1$ is branched or unbranched, alkyl, alkenyl or alkynyl of from 1 to 5 carbons, and A$_1$ is unsubstituted or substituted independently with one or more substitutions of OH, SH, NH$_2$ or halide, a branched or unbranched, alkyl, alkenyl or alkynyl of from 1 to 6 carbons, unsubstituted or substituted independently with one or more substitutions of OH, SH, NH$_2$ or halide, or a 5-, 6-, or 7-membered first ring, saturated or unsaturated, unsubstituted or substituted independently with one or more substitutions of (a) OH or (b) a branched or unbranched, alkyl, alkenyl or alkynyl of from 1 to 6 carbons, unsubstituted or substituted independently with one or more substitutions of OH, SH, NH$_2$ or halide, where the 5-, 6-, or 7-membered first ring is carbocyclic or heterocyclic with one to two heteroatoms of O, N, or S;

R$_2$ and R$_6$ are independently H, OH, SH, NH$_2$, halide, A$_2$ where A$_2$ is alkyl, alkoxy, alkenyl, alkenoxy, alkynyl, or alkynoxy, or alkanol, alkenol, or alkynol of one or more, OH moieties on the alkanol, alkenol, or alkynol, where A$_2$ is unbranched or branched, of from 1 to 4 carbons, and A$_2$ is unsubstituted or substituted independently with one or more substitutions of NH$_2$, COOH, halide, SH, OH, or guanidinium;

R$_3$ is COO$^-$, POO$^-$, BOO$^-$ or SOO$^-$ where the corresponding cation is H or a salt; and wherein A) R$_4$ is H and R$_5$ is NO$_2$;

B) R$_4$ is H, OH, SH, halide, COOH, guanidinium, or alkanol of one or more OH moieties, branched or unbranched, of from 1 to 4 carbons, and R$_5$ is A$_3$ where A$_3$ is alkyl, alkoxy, alkenyl, alkenoxy, alkynyl, or alkynoxy, or alkanol, alkenol, or alkynol of one or more OH moieties on the alkanol, alkenol, or alkynol, where A$_3$ is unbranched or branched, of from 1 to 4 carbons, and A$_3$ is unsubstituted or substituted independently with one or more substitutions of NH$_2$, COOH, halide, SH, OH, or guanidinium; or C) R$_4$ is C, CH, or CH$_2$ and R$_5$ is CH, or CH$_2$, R$_4$ forms a 4-, 5-, or 6-membered second ring with R$_5$, where the second ring is saturated, partially unsaturated or fully unsaturated, carbocyclic or heterocyclic with one to two heteroatoms of O, N, or S substituted for any second ring carbon, and R$_4$ is unsubstituted or is substituted independently with one or more substitutions of OH or alkanol, alkenol, or alkynol of one or more OH moieties on the alkanol, alkenol, or alkynol, branched or unbranched, of from 1 to 4 carbons, and R$_5$ is substituted with A$_4$NH$_3^+$, where A$_4$ is alkyl, alkenyl or alkynyl, or alkanol or alkenol of one or more OH moieties on the alkanol or alkenol, of from 1 to 3 carbons, and, for the 5- or 6-membered second ring, the intermediate second ring carbons between R$_4$ and R$_5$ are independently unsubstituted or substituted with one or more substitutions of OH, or alkanol, alkenol or alkynol of one or more OH moieties on the alkanol, alkenol, or alkynol, branched or unbranched, of from 1 to 4 carbons; or an analog, pharmaceutically acceptable salt, or derivative of the inhibitor of the formula I.

12. The method of claim 11, wherein R$_4$ is H and R$_5$ is NO$_2$.

13. A method of treating bacterial or trypanosomal infection, comprising administering to a subject in need thereof a treatment effective amount of a compound of formula I:

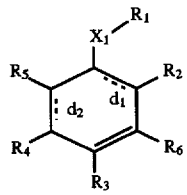
(I)

wherein the dashed lines $d_1$ and $d_2$ are independently unsaturations or saturations and the core ring is carbocyclic or heterocyclic with one to two heteroatoms of O, N, or S;

$X_1$ is CO, $SO_2$, NH, $CH_2$, S, or ();

$R_1$ is $NH_2$, SH, $OCH_3$, halide,

COA$_1$, where $A_1$ is branched or unbranched, alkyl, alkenyl or alkynyl of from 1 to 5 carbons, and $A_1$ is unsubstituted or substituted independently with one or more substitutions of OH, SH, $NH_2$ or halide, a branched or unbranched, alkyl, alkenyl or alkynyl of from 1 to 6 carbons, unsubstituted or substituted independently with one or more substitutions of OH, SH, $NH_2$ or halide, or a 5-, 6-, or 7-membered first ring, saturated or unsaturated, unsubstituted or substituted independently with one or more substitutions of (a) OH or (b) a branched or unbranched, alkyl, alkenyl or alkynyl of from 1 to 6 carbons, unsubstituted or substituted independently with one or more substitutions of OH, SH, $NH_2$ or halide, where the 5-, 6-, or 7-membered first ring is carbocyclic or heterocyclic with one to two heteroatoms of O, N, or S;

$R_2$ and $R_1$ are independently H, OH, SH, $NH_2$, halide, $A_2$ where $A_2$ is alkyl, alkoxy, alkenyl, alkenoxy, alkynyl, or alkynoxy, or alkanol, alkenol, or alkynol of one or more OH moieties on the alkanol, alkenol, or alkynol, where $A_2$ is unbranched or branched, of from 1 to 4 carbons, and $A_2$ is unsubstituted or substituted independently with one or more substitutions of $NH_2$, COOH, halide, SH, OH, or guanidinium; p1 $R_4$ is $COO^-$, $POO^-$, $BOO^-$ or $SOO^-$ where the corresponding cation is H or a salt; and wherein A) $R_4$ is H and $R_5$ is $NO_2$;

B) $R_4$ is H, OH, SH, halide, COOH, guanidinium, or alkanol of one or more OH moieties, branched or unbranched, of from 1 to 4 carbons, and $R_5$ is $A_3$ where $A_3$ is alkyl, alkoxy, alkenyl, alkenoxy, alkynyl, or alkynoxy, or alkanol, alkenol, or alkynol of one or more OH moieties on the alkanol, alkenol, or alkynol, where $A_3$ is unbranched or branched, of from 1 to 4 carbons, and $A_3$ is unsubstituted or substituted independently with one or more substitutions of $NH_2$, COOH, halide, SH, OH, or guanidinium; or C) $R_4$ is C, CH, or $CH_2$ and $R_5$ is CH, or $CH_2$, and $R_4$ forms a 4-, 5-, or 6-membered second ring with $R_5$, where the second ring is saturated, partially unsaturated or fully unsaturated, carbocyclic or heterocyclic with one to two heteroatoms of O, N, or S substituted for any second ring carbon, and $R_4$ is unsubstituted or is substituted independently with one or more substitutions of OH or alkanol; alkenol, or alkynol of one or more OH moieties on the alkanol, alkenol, or alkynol, branched or unbranched, of from 1 to 4 carbons, and $R_5$ is substituted with $A_4NH_3^+$, where $A_4$ is alkyl, alkenyl or alkynyl, or alkanol or alkenol of one or more OH moieties on the alkanol or alkenol, of from 1 to 3 carbons, and, for the 5- or 6-membered second ring, the intermediate second ring carbons between $R_4$ and $R_5$ are independently unsubstituted or substituted with one or more substitutions of OH, or alkanol, alkenol or alkynol of one or more OH moieties on the alkanol, alkenol, or alkynol, branched or unbranched, of from 1 to 4 carbons; or an analog, pharmaceutically acceptable salt, or derivative of the inhibitor of the formula L 14. The method of claim 13, wherein $R_4$ is H and $R_5$ is $NO_2$.

* * * * *